(12) United States Patent
Margulis et al.

(10) Patent No.: US 6,259,944 B1
(45) Date of Patent: Jul. 10, 2001

(54) SYSTEM AND METHOD FOR MONITORING ACTIVITY

(75) Inventors: Eliahu Margulis, Oranit; Alexander Frank, Ramat-Gan, both of (IL)

(73) Assignee: Pylon, Inc (VG)

( * ) Notice: Subject to any disclaimer, the term of this patent is extended or adjusted under 35 U.S.C. 154(b) by 0 days.

(21) Appl. No.: 09/209,596

(22) Filed: Dec. 11, 1998

(30) Foreign Application Priority Data

Dec. 14, 1997 (IL) .................................................. 122597

(51) Int. Cl.[7] ............................ A61B 5/04; A61B 5/0432
(52) U.S. Cl. ........................ 600/509; 600/520; 600/523; 128/903
(58) Field of Search ........................... 128/903; 600/509, 600/519, 520, 523

(56) References Cited

U.S. PATENT DOCUMENTS

| 3,639,907 | * | 2/1972 | Greatbach . | |
| 3,724,455 | * | 4/1973 | Unger . | |
| 4,121,573 | | 10/1978 | Crovella et al. . | |
| 4,566,461 | | 1/1986 | Lubell et al. . | |
| 5,157,604 | * | 10/1992 | Axford et al. . | |
| 5,474,090 | * | 12/1995 | Begun et al. . | |
| 5,640,965 | | 6/1997 | Maeyama . | |
| 5,718,234 | * | 2/1998 | Warden et al. | 128/903 |
| 5,907,291 | * | 5/1999 | Chen et al. | 600/509 |
| 5,944,659 | * | 8/1999 | Flach et al. | 600/300 |

FOREIGN PATENT DOCUMENTS

| 2259772 | 3/1993 | (GB) . |
| 8602538 | 5/1986 | (WO) . |
| 9626495 | 8/1996 | (WO) . |
| 9712546 | 4/1997 | (WO) . |
| 9718639 | 5/1997 | (WO) . |

* cited by examiner

*Primary Examiner*—Carl H. Layno
(74) *Attorney, Agent, or Firm*—Jones, Day, Reavis & Pogue

(57) ABSTRACT

A system for simultaneous monitoring of a plurality of individuals including an individual physiological data logger (IPDL) for each individual for measuring and storing heart beat data, the IPDL including: an electro-cardiogram (ECG) measuring device for providing heart beat data, an extended memory for storing the measured heart beat data, a synchronization element, a micro-controller including a synchronization element controlling circuit, and RF transceiver apparatus; a central interface unit selectably couplable by radio telemetry communication to each IPDL for transmitting thereto a plurality of commands and for receiving therefrom the heart beat data; and a computer coupled to the central interface unit for providing commands for each IPDL, for performance of an individual bench test for deriving a conversion coefficient of heart beat cost per unit of mechanical work, and for monitoring and analyzing, in real time, the heart beat data of each of the plurality of individuals.

29 Claims, 15 Drawing Sheets

SYSTEM AND METHOD FOR MONITORING ACTIVITY

FIELD OF THE INVENTION

The present invention relates to a fully computerized telemetry system for monitoring the activity level and the physiological status of an individual, or a group of individuals performing various exercises.

BACKGROUND OF THE INVENTION

There are many methods known in the art for monitoring the activity of an individual during exercise of many kinds. Some of these are used for physiological purposes, e.g., so-called stress tests, while others are used to monitor individuals or groups during training sessions, such as bio-feedback for sports players.

In particular, measurement of heart rate has been used frequently as an indication of the amount of work performed by an individual during a given activity. A number of devices are known for monitoring heart rate and analyzing the data produced thereby. For example, there is shown in U.S. Pat. No. 4,566,461 to Lubell et al, a heart rate monitor device for use in monitoring aerobic exercise training, which automatically calculates a fitness parameter for the subject through an exercise stress test protocol.

There is shown in U.S. Pat. No. 4,958,645 to Cadell et al. a medical radio telemetry system having a plurality of telemeters, one located on each patient for collecting data such as temperature, heart rate, respiration rate, blood pressure level, etc. The patient telemeter works includes a patient locator and works in conjunction with a room locator for monitoring by a receiver.

There is shown in U.S. Pat. No. 5,157,604 to Axford et al. an apparatus for simultaneously monitoring the heart rate of each of a plurality of subjects including a main circuit for transmitting a predetermined signal to cause each of a plurality of remote subcircuits to transmit subcircuit identity data and heart rate data, a receiver for receiving these transmissions and producing an output representative of the heart rate, and a plurality of remote subcircuits, each having a pulse monitoring device for securing to a subject.

None of these devices permits real time monitoring of exercise programs individually tailored for each of a large group of individuals for use by a coach or physiologist and which permits analysis of past and present training sessions.

SUMMARY OF THE INVENTION

According to the present invention, there is provided a system for simultaneous monitoring of a plurality of individuals including an individual physiological data logger (IPDL) for each individual for measuring and storing heart beat data, the IPDL including: an electro-cardiogram (ECG) measuring device for providing heart beat data, an extended memory for storing the measured heart beat data, a synchronization element, a micro-controller including a synchronization element controlling circuit, and RF transceiver apparatus; a central interface unit selectably couplable by radio telemetry communication to each IPDL for transmitting thereto a plurality of commands and for receiving therefrom the heart beat data; and a computer coupled to the central interface unit for providing commands for each IPDL, for performance of an individual bench test for deriving a conversion coefficient of heart beat cost per unit of mechanical work, and for monitoring and analyzing, in real time, the heart beat data of each of the plurality of individuals.

According to a preferred embodiment of the invention, the computer further includes means for analyzing and storing data about each individual over time.

There is also provided in accordance with the present invention a method for monitoring the activity level and the physiological status of an individual, or a group of individuals, including the steps of measuring heart beat pulses in an IPDL worn adjacent the chest of an individual, calculating heart beat data in the IPDL, storing the heart beat data in the IPDL, transmitting a command via RF transceiver apparatus from a central interface unit (CIU) to the IPDL in response to a command to transmit the stored heart beat data, transmitting the stored heart beat data via RF transceiver apparatus from the IPDL to the CIU, transferring the heart beat data from the CIU to a computer, analyzing and processing the heart beat data in the computer in real time utilizing an individual coefficient of heart beats cost per unit of external work, and providing an output display, in real time, corresponding thereto.

According to a preferred embodiment, the method further includes the steps of providing a graphic presentation of the analyzed heart beat data.

According to one embodiment of the invention, the computer begins recording data of a session for a plurality of individuals upon an input command, and heart beat data for each individual is stored in association with session identification data.

According to another embodiment of the invention, the method further includes the steps of coupling an unused IPDL to a new individual, measuring and storing heart beat data for the new individual in the IPDL, starting a monitoring session for the new individual in the computer, and causing the computer to actuate the CIU to request transmission of the stored heart beat data from the IPDL, without interrupting other existing sessions.

According to a further embodiment of the invention, the method further includes the steps of removing an IPDL from one of the plurality of individuals, and ending the monitoring session for that individual in the computer, without interrupting other existing sessions, and closing, on a monitor screen, a client window associated with the individual.

According to an alternative embodiment of the invention, the IPDL provides heart beat data together with heart beat identification data, the computer scans the heart beat identification data during analysis and commands the CIU to request re-transmission of any missing heart beat data.

BRIEF DESCRIPTION OF THE DRAWINGS

The present invention will be further understood and appreciated from the following detailed description taken in conjunction with the drawings in which.

DETAILED DESCRIPTION OF THE INVENTION

The present invention relates to a fully computerized RF telemetry system for monitoring the activity level and the physiological status of an individual, or of a group of individuals performing various exercises. It is a particular feature of the invention that the system can be used by a coach, trainer or physiologist to aid in determining an appropriate or optimal exercise program for each individual, based on his or her own physical fitness level. Thus, the individual program can be changed as the fitness of the individual changes. The system is based on measuring heart beats and analyzing these data to calculate total heart beat cost for the individual while performing specific mechanical work. This measure is used later during the individual's exercise sessions. It is a particular feature of the present invention that it can also be used to monitor the fitness and performance level of animals, particularly horses, as well as human beings.

Figure 1:
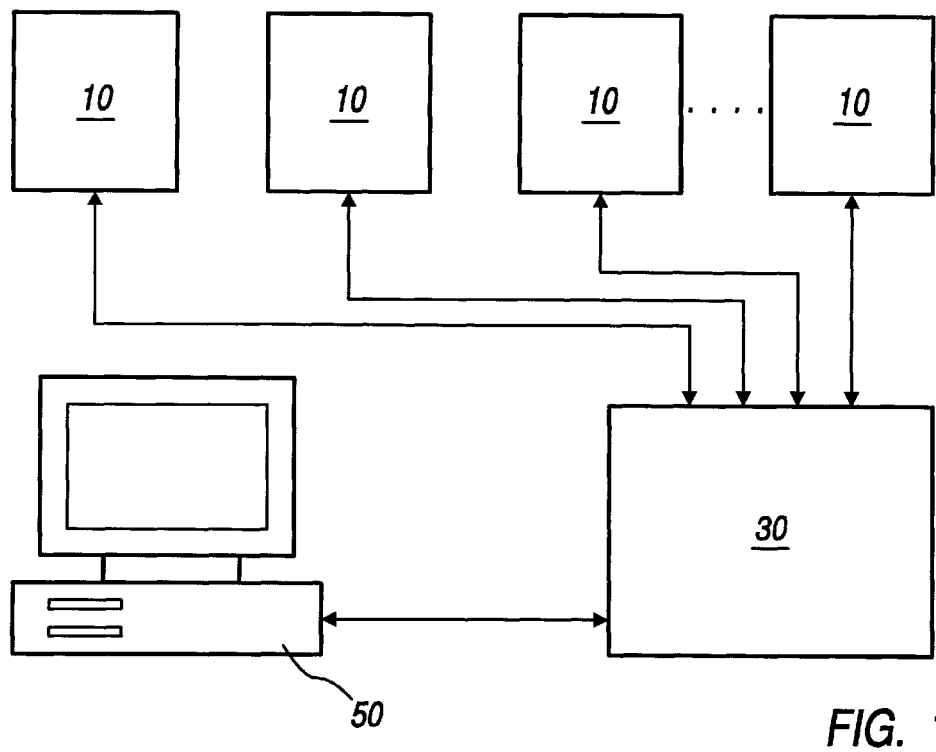
FIG. 1 is a schematic illustration of the monitoring system of the present invention.

As seen in FIG. 1, a schematic illustration of the monitoring system of the present invention, the system includes at least one individual physiological data logger (IPDL) 10 for measuring heart beats, a central interface unit 30 coupled by RF transceiver apparatus to each IPDL, and a computer 50, here illustrated as a personal computer (PC), for monitoring and analysis of the heart beat data, both in real time and over time.

IPDL 10 is an individual unit, worn on the chest of the individual, which measures the individual's heart beats by measuring electrical changes on the chest, as known. IPDL 10 includes a memory for storing heart beat data for a period of time, as described in detail hereinbelow. Each IPDL has its own identification number, such as the manufacturer's serial number, printed on it at the time of manufacture and programmed permanently into it. This number is used to identify the IPDL in its communications with the system.

Central interface unit (CIU) 30 includes a processor for receiving the heart beat data, in turn, from each IPDL, and for transferring the data to a computer 50, which simultaneous monitors the heart beats, and the corresponding physical state, in real time, of a plurality of individuals performing a variety of exercises. Computer 50 also analyzes, off line, the heart beat data for each individual over time.

It is a particular feature of the present invention that a number of individuals, for example 25, each wearing his own IPDL, can be simultaneously monitored by the system, in real time, each performing his own activities during his own independent session. As stated above, the preferred embodiment of the system of the present invention permits a trained physical fitness professional, whether coach or physiologist, to observe vital statistics, simultaneously, of a plurality of individuals, each working at his or her own pace and using an individually tailored exercise plan. The plan can be changed during an exercise session if the coach or physiologist sees a deterioration of the individual's physical condition, or if the individual is not working up to capacity. Individuals can easily be added to, or removed from, the group during each training session, since the data for each is recorded in his own independent computer session. No conventional system permits such flexibility or such monitoring, in real time, with no loss of data between the individual and the system.

Figure 2:
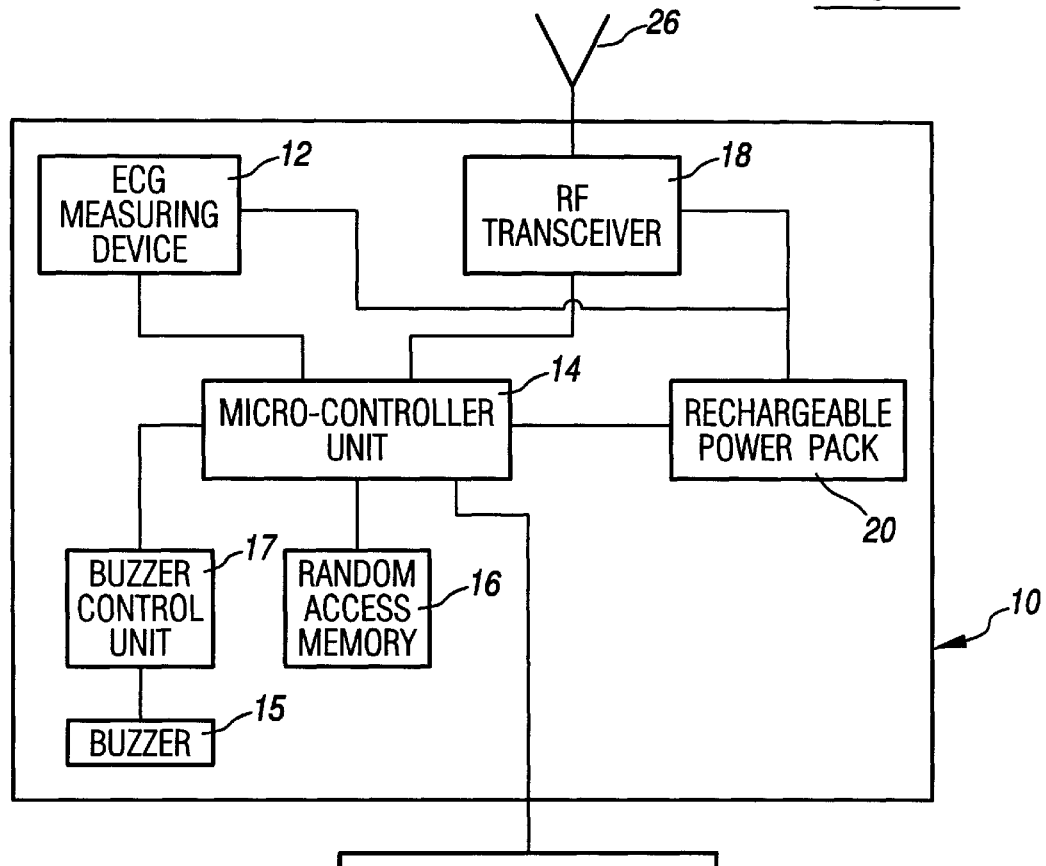
FIG. 2 is a block diagram illustration of an individual data logger for use in a preferred embodiment of the invention.

Referring now to FIG. 2, there is shown a block diagram illustration of an individual physiological data logger (IPDL) 10 according to a preferred embodiment of the invention. IPDL 10 includes an ECG (electro-cardiogram) measuring device 12, which is preferably a printed circuit board, for measuring electrical activity of the heart muscle as detectable on the chest, as known.

ECG measuring device 12 is coupled to a micro-controller unit 14. Micro-controller unit 14 includes an extended memory, for example a Random Access Memory (RAM) or a flash memory 16, a clock for providing time marks, and software for operating RF transceiver apparatus 18 for RF communication with central interface unit (CIU) 30. IPDL 10 provides heart beat data in one of two forms, either as time marks, i.e., the absolute time from the start of exercise, according to the clock, at which a heart beat pulse signal is received, or as relative time intervals between each heart beat, together with heart beat identification data. In the latter case, each measured heart beat is numbered consecutively, or identified in another way, so that it can easily be determined whether any heart beat data has not been received in computer 50. If it is determined that some heart beat data has not been received, the computer commands the CIU to request re-transmission of the missing heart beat data. This heart beat data is stored in the IPDL buffer (memory).

The micro-controller unit 14 manages a number of functions. It manages the two way, half-duplex RF communication between the IPDLs and the CIU 30, heart beat storage upon command from the computer program, providing an audible signal at the start and stop of exercises, and synchronization of rhythmical beeping during the Bench Test (described below), among others.

It is a particular feature of the invention that IPDL 10 includes an extended memory. This provides great flexibility to the system for securing acquisition of heart beat data, despite possible breaks in RF communication, and for individual home training work and subsequent transmission of accumulated data to the system upon request by the coach via the computer.

IPDL 10 is also provided with a synchronization element 15, here illustrated as a buzzer, and an associated synchronization element control unit 17. Synchronization element 15 serves to provide synchronization pulses, which are preferably audible signals, but can alternatively be any other signal, which provides a beat or other indication to the wearer of the rate at which to perform a task. This is used in the Bench Test, described in detail hereinbelow.

IPDL 10 also includes an electric power source 20, preferably a rechargeable power cell, possibly with an associated DC/DC converter, for powering all the IPDL circuits, namely, the ECG measuring device, micro-controller, RF transceiver, and synchronization element and control unit.

It is a particular feature of the present invention that the system monitors heart beat interval data, and the total heart beats cost of work, which is the actual power expended by an individual throughout the work performed, including warm-up time and resting time, rather than merely the heart beat rate (an average of the number of heart beats per unit time). The variability of heart rate, as analyzed through spectral analysis, reflects various physiological processes in the body. Calculation of heart beat intervals, rather than merely average heart beat rate, permits the spectral analysis of the variability of the heart beat which, in turn, permits the trainer to evaluate the effects of exercise and stress on the body. The use of fast Fourier transform in the present invention provides such spectral analysis by computer 50 for use by the trainer in the training sessions. In addition, by studying heart beat interval data, it is possible to discover arrythmias and other heart irregularities, which cannot be found by looking at the average heart rate.

Heart beats cost is the actual cost to the body of an individual of performing specific, measured mechanical work, i.e., walking up stairs, which involves lifting the body weight up the height of each stair, and corresponds to the energy cost (KCal expended). However, unlike the supposed work done by operating a machine, for instance, an exercise bicycle, where a certain caloric expenditure is anticipated for a certain period of riding at a certain speed, the present system measures actual work done by the individual, including the cost of physiological changes in the body. (For example, lifting a weight on a hot day requires more work (higher heart beats cost) than lifting the same weight on a cool day.) Furthermore, the heart beats during warm-up and restitution (before and after the mechanical work) are also included in the calculation of heart beats cost, thereby providing a total cost which is equal to the total number of heart beats above the heart rate at rest. Thus, heart beats cost depends on the age, gender, and fitness of the individual. This heart beats cost of work is more accurate in evaluating performed work than heart rate as calculated in conventional systems.

It is the goal of the individual training plan to cause the individual to reach a target heart beats cost or percentage of the maximum heart beats cost during each session. Since heart beats cost decreases with increasing fitness, the present method permits dynamic monitoring of the fitness of the individual, and the training program can be modified in accordance with actual progress. Thus, the present invention is useful not only for sports training and other exercise groups, but also for individuals and groups for weight control, increasing physical fitness, etc.

Figure 3:
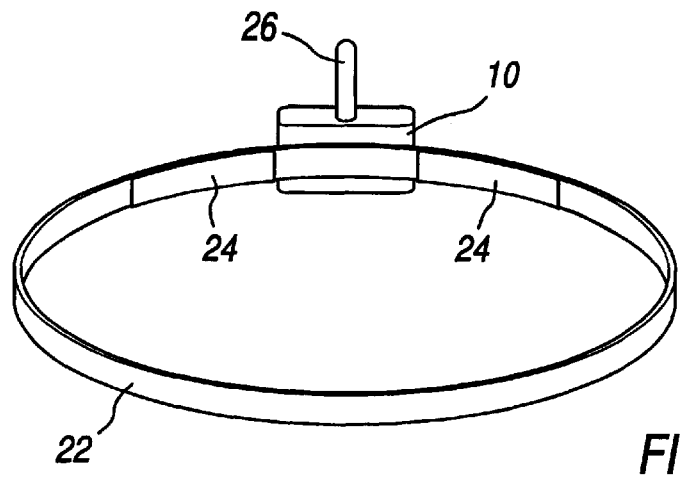
FIG. 3 is a schematic perspective illustration of the logger of FIG. 2 ready for wearing.

IPDL 10 is removably mounted on an elastic belt 22, shown in rear perspective view in FIG. 3, for wearing on the chest of the user. Elastic belt 22 includes two electrodes 24 arranged to contact two points located symmetrically about the longitudinal axis of the user's chest, as seen schematically in FIG. 3. The other ends of electrodes 24 are coupled to the ECG measuring device, as known. An antenna 26 may be coupled to the IPDL casing for RF transmission and reception. Preferably, IPDL 10 also includes a reset button (not shown) to permit actuation of the IPDL by the user.

Figure 4:
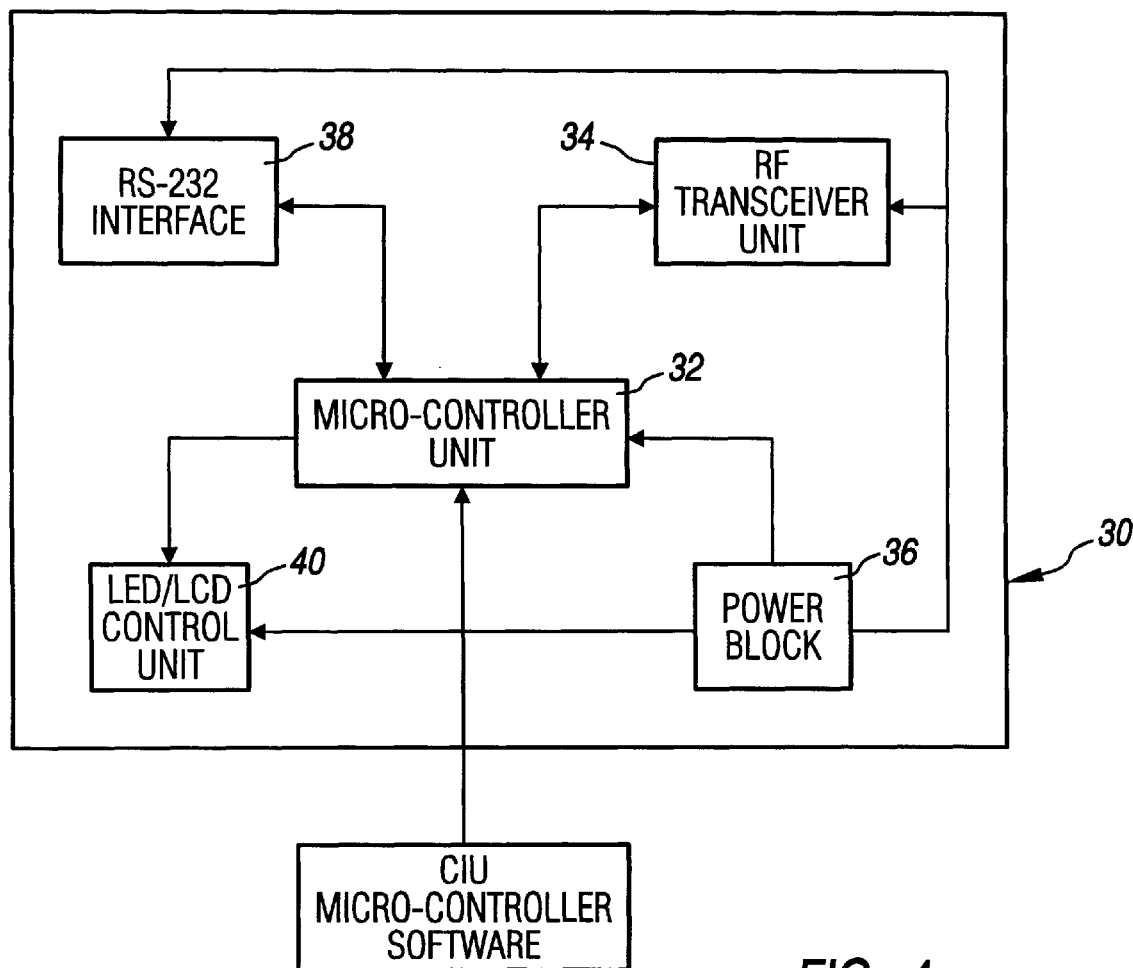
FIG. 4 is a block diagram illustration of a central interface unit according to a preferred embodiment of the invention.

Referring now to FIG. 4, there is shown a block diagram illustration of a central interface unit (CIU) 30 according to a preferred embodiment of the invention. CIU 30 includes a micro-controller 32, RF transceiver apparatus 34 for communication with the IPDLs, and a power source 36, such as a rechargeable battery cell, possibly with an associated DC/DC converter. According to one embodiment of the invention, CIU 30 also includes an RS-232 interface 38 or other communication circuit for coupling to computer 50, and a display 40, such as an LED or LCD function display. LED display 40 indicates that there is proper communication and proper data flow from each IPDL. CIU 30 is preferably a light weight, portable device.

Micro-controller 32 of CIU 30 coordinates the radio-telemetric net management of all the IPDLs, including data request sending and data block receiving. It is responsible for heart beat data acquisition, and for transferring current system data to computer 50, such as via a serial or parallel comunication port. Micro-controller 32 includes software, described in detail below, for pooling the group by requesting and receiving data from each IPDL in turn. It will be appreciated that each IPDL can have equal transmission time, fixed in advance, or the transmission time can be flexible, the transmission time of each IPDL depending on the quantity of data to be transmitted.

Transceiver apparatus 34 provides a stable RF half-duplex digital data channel between CIU 30 and each IPDL 10. At present, apparatus 34 provides RF communication for a distance of some 200 meters and more.

Computer 50 can be any suitable computer, and is preferably a personal computer, version 486 or higher. A particularly suitable computer is a Pentium 586 portable lap-top computer. For ease of discussion in the specification only, computer 50 will be referred to hereinbelow as a PC (personal computer).

Figure 5:
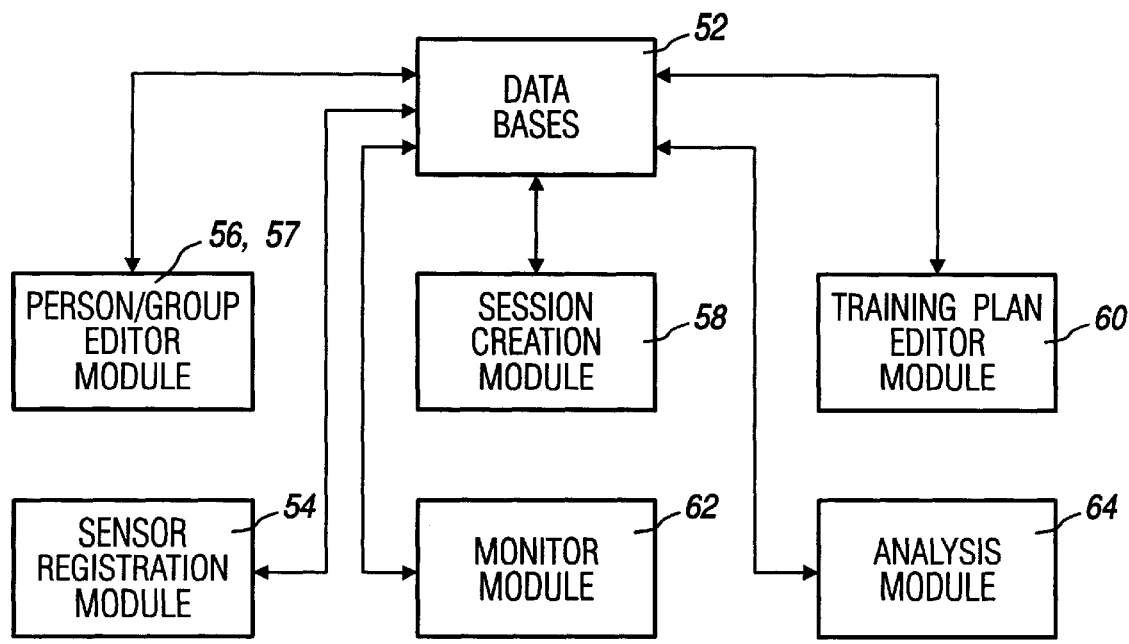
FIG. 5 is a block diagram illustrating a general PC program arrangement according to a preferred embodiment of the present invention.

FIG. 5 is a block diagram illustrating a general PC program arrangement according to a preferred embodiment of the present invention. The program is based on a plurality of data bases 52 and a variety of software modules, each dealing with a different aspect of the system. According to the illustrated embodiment, the following data bases are created: a Personal Data Base, an individual and physical data base for each training person; a Fitness Data Base, including fitness data for each individual; a Groups Data Base, for each group which trains together; a Sensor Data Base, for data about each IPDL; a Training Session Plans Data Base, including various plans for individual and group training sessions; a Sessions Data Base, for details about each session; a Heart Beat Time Marks Data Base, including heart beat data for each individual; a Manual Coach Markers Data Base, including selected time marks for each individual inserted by the trainer or coach; and an Exercises Data Base, including the various exercises from which each training plan is built.

The software modules preferably include a Sensor Registration Module 54, a Person Editor Module 56, a Group Editor Module 57, a Session Creation Module 58, a Training Plan Editor Module 60, a Monitor Module 62, and an Analysis Module 64.

Figure 6:
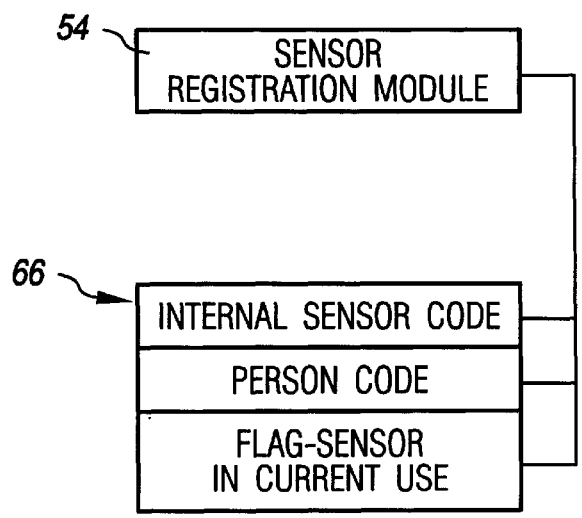
FIG. 6 is a block diagram illustration of a sensor registration module according to the invention.

Sensor Registration Module 54, illustrated in more detail in FIG. 6, permits creation and editing of a sensor data base 66 including an internal sensor code. The internal sensor code is a permanent identification code, such as the manufacturer's identification number, which is used to identify a particular IPDL and to associate it with the person code, or identification details, of the individual wearing that IPDL during a particular session. In order to prevent a single IPDL being assigned to two individuals, a flag can be provided on the screen indicating that the IPDL is in use.

When the IPDL is first used in the system, its internal identification number is entered into the sensor data base as the internal sensor code, for later reference by the CIU and PC.

Figures 7, 8:
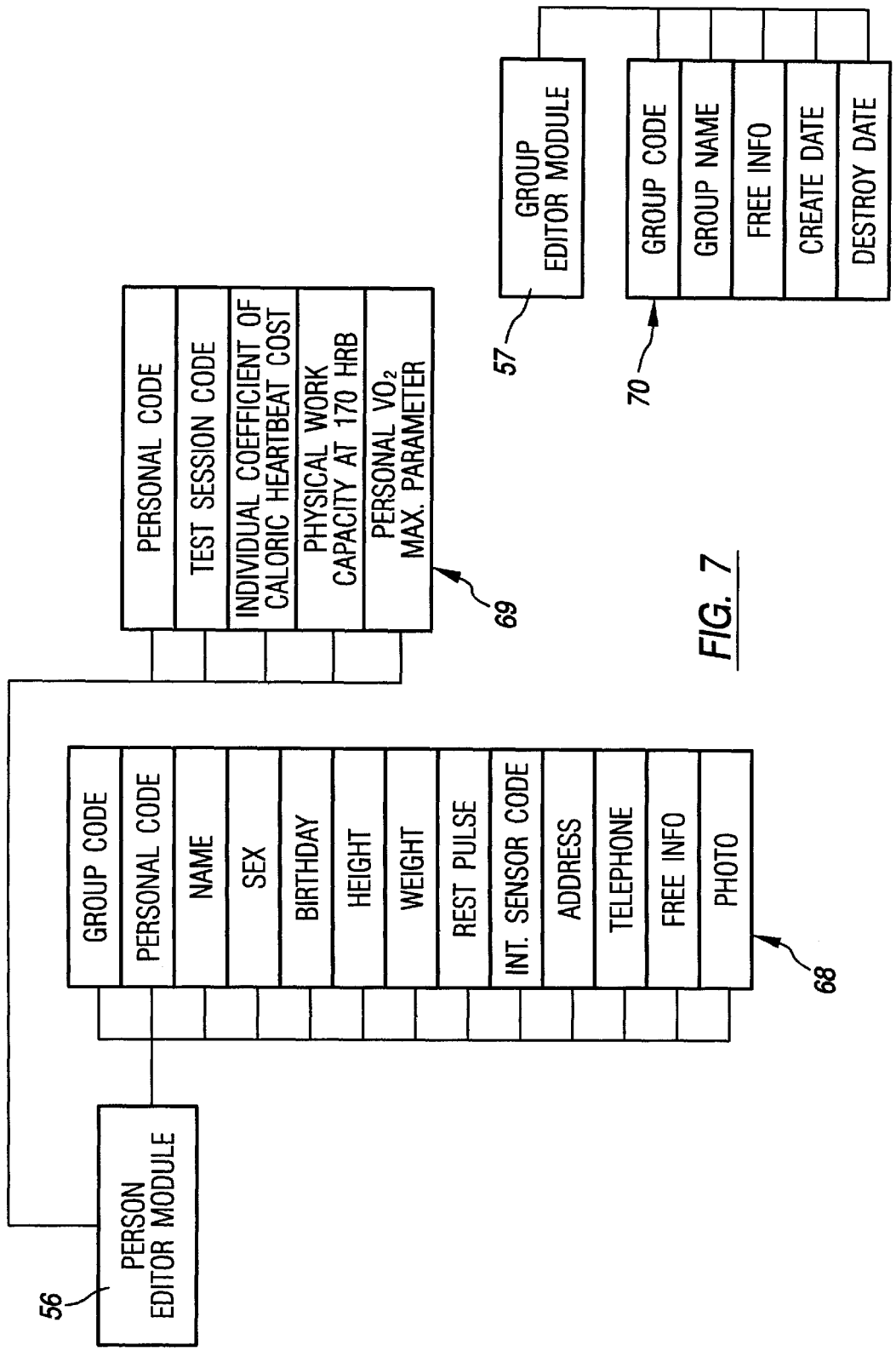
FIG. 7 is a block diagram illustration of a person editor module according to the invention.
FIG. 8 is a block diagram illustration of a group editor module according to the invention.

The Person Editor Module 56, shown in detail in FIG. 7, permits editing of a Personal data base 68 which includes personal data about each individual who participates in exercise programs on the network. When an individual begins to work-out using the system, he is assigned a personal code for identifying him within the system. His personal details, including name, sex, birthday, height, weight, address, and telehone number are entered into the Personal Data base together with his personal code, and any other information the individual cares to give, including a photo. A group or session code identifying each session he attends can also be stored with the individual's personal data.

The individual's rest pulse is measured and entered in the data base. Then, the individual is given a test, such as the so-called Bench Test, to determine a test pulse while doing a measurable amount of external work. From these, his individual conversion coefficient for cost of work (heart beats cost) is calculated. These data are entered in a Personal Fitness Data Base 69. Personal Fitness Data Base 69 includes the personal code of each individual, together with a test session code, the individual coefficient of caloric heart beats cost, a physical working capacity calculation, and a fitness coefficient ($VO_2$ Max).

The Group Editor Module 57, shown in detail in FIG. 8, permits creation and editing of a Group Data Base 70 which permits identification, for purposes of monitoring and analysis, of each group of individuals who plan to exercise together. The group is assigned a group code, which is stored with each individual who belongs to that group, and preferably a group name, for ease of reference. Information about the group, i.e., "Maccabee Basketball Team—January 1997", can be entered for more precise identification of the group. The dates the group was created and disbanded are also stored in the data base.

Figures 9, 10:
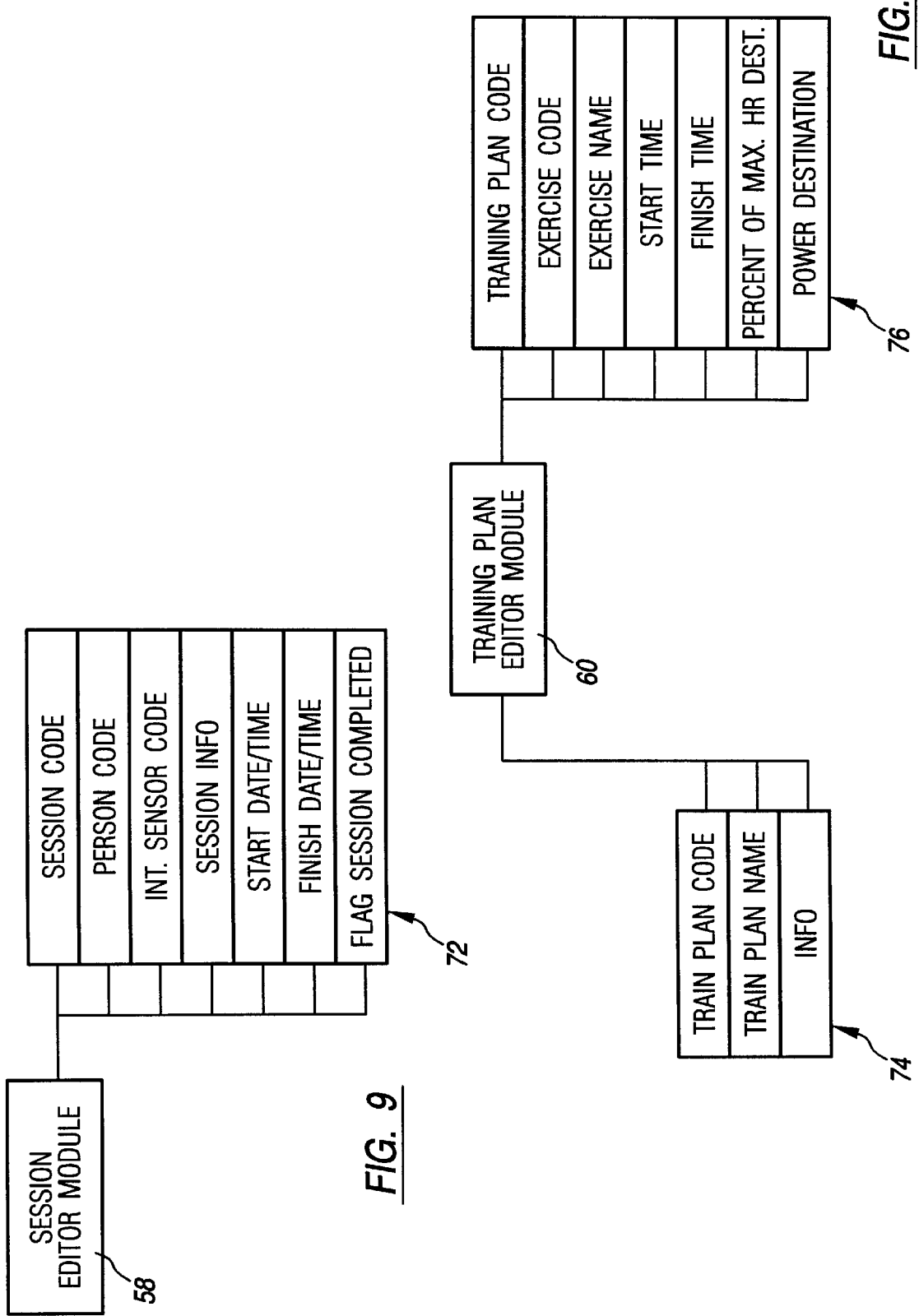
FIG. 9 is a block diagram illustration of a session editor module according to the invention.
FIG. 10 is a block diagram illustration of a training plan editor module according to the invention.

Session Editor Module 58, shown in detail in FIG. 9, includes a Sessions Data base 72 for identifying each session monitored or analyzed by the system. Each time an individual begins a training session, a computer session corresponding to that session starts. Each session is assigned a session code and saved together with the person code of the individual and the internal code of the sensor. Information about the session can be included. The date and time the session began and ended are also saved.

Thus, the Personal and Group Editor Modules, together with the Session Editor Module, provide great flexibility for the system. New personal data can be input and edited, different groups can easily be arranged, an IPDL number for the session can be assigned to a specific person, and personal physiological parameters, such as weight, height, and a personal fitness parameter, can be calculated and followed over a long time period.

It is a particular feature of the invention that additional persons can be added to or removed from the monitoring system during a training session without affecting monitoring of any other individual. This is due to the fact that a separate monitoring session is begun and recorded for each individual each time he begins training.

Training Plan Editor Module 60, shown in detail in FIG. 10, utilizes two data bases, a Training Plans Data base 74 and an Exercise Data base 76. The Training Plan Editor module permits a coach or physiologist to tailor an exercise program for each individual, and to set the maximum and optimum activity levels for that individual during that program. The coach can assign a particular training drill to an entire sessional group. The system can support direct monitoring of the individual, i.e., on-line control during the exercise process according to physiological parameters, such as highest or lowest heart beat rate, etc. It can also support monitoring in accordance with a predetermined training plan. In this case, each individual has his or her own plan, including time table, schedule of exercises, etc., which may or may not be the same as the plan of anyone else in the group.

The Training Plans Data base 74 includes detailed information about each training plan, stored together with a training plan code and training plan name.

The Exercise Data base 76 includes a plurality of exercises which can be used in each training plan. The Exercise code and name for each exercise are stored in the data base with the training plan code for each individual. Start time and Finish time are recorded together with the individual's cost of work goal, and the desired percent of maximum heart rate.

According to a preferred embodiment of the invention, each training program includes a combination of specific external work, consisting of different sport activities, such as walking, running, resting, cycling, etc., over different periods of time. When a particular training program is assigned to a specific individual, the external work values are automatically converted to personal heart beats cost, using the individual coefficient stored in the Personal Fitness Data Base, and displayed in a personal Monitoring Window, as a personal target power expenditure during the session.

Figure 11:
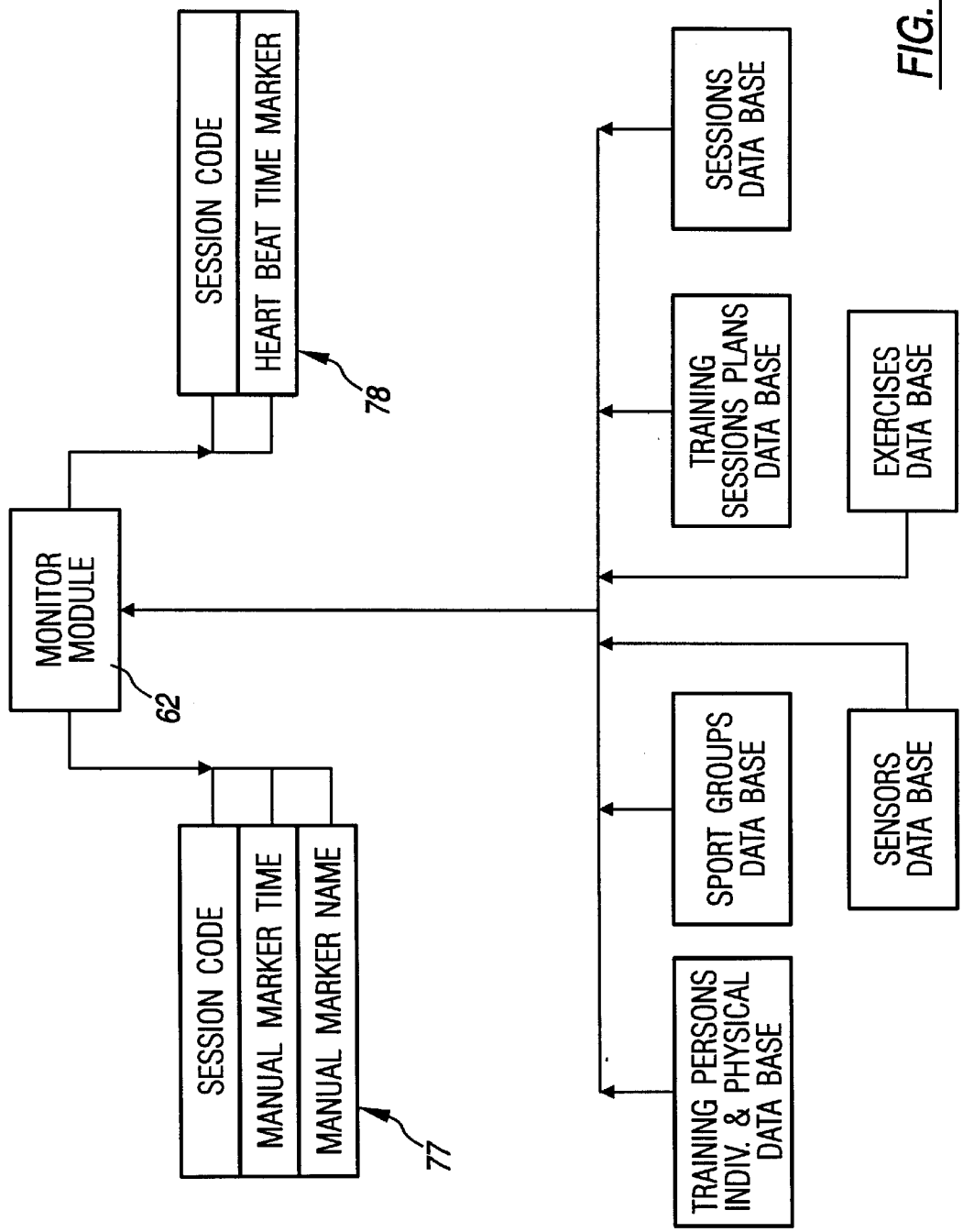
FIG. 11 is a block diagram illustration of a monitor module according to the invention.

Monitor Module 62, illustrated in detail in FIG. 11, has access to all the other data bases and controls the real time monitoring of all individuals in the group. From the various data bases, monitor module 62 forms a Manual Markers data base 77 and a Heart Beat Time Marks data base 78. Markers are visible or audible indicators which appear on the display during the session, to indicate external events or internal changes during the training session. For example, when the total desired heart beat cost for an individual is reached, a marker is provided, so the coach can tell the individual to stop exercising. Alternatively, when an irregularity in heart beat is detected, a marker is provided so the coach or physiologist can examine the individual. Similarly, it is generally desirable to insert markers to indicate when drill time has elapsed, when it is time to change to a different exercise, when the battery is low and should be charged, and when the individual is out of radio contact. It will be appreciated that some of these markers are automatically inserted by the processor of the monitor in accordance with the individual's personal data, and others are inserted by the coach and can be changed, as desired. The appearance of these markers, and the absolute time at which they appeared, will also be recorded in the session data base, together with all the other data about the session.

Thus, the Manual Markers data base includes the session code for the particular session, which is specific to a single individual who is exercising, and one or more manual markers, including marker time and marker name.

In the illustrated embodiment, the Heart Beat Time Marks data base is the data base including all the heart beat data for the individual. It also includes session code to identify the individual and the particular session. This data can be viewed in graphical and statistical form by a coach in real time, on line, by opening the window of the selected individual on the screen.

Figure 12:
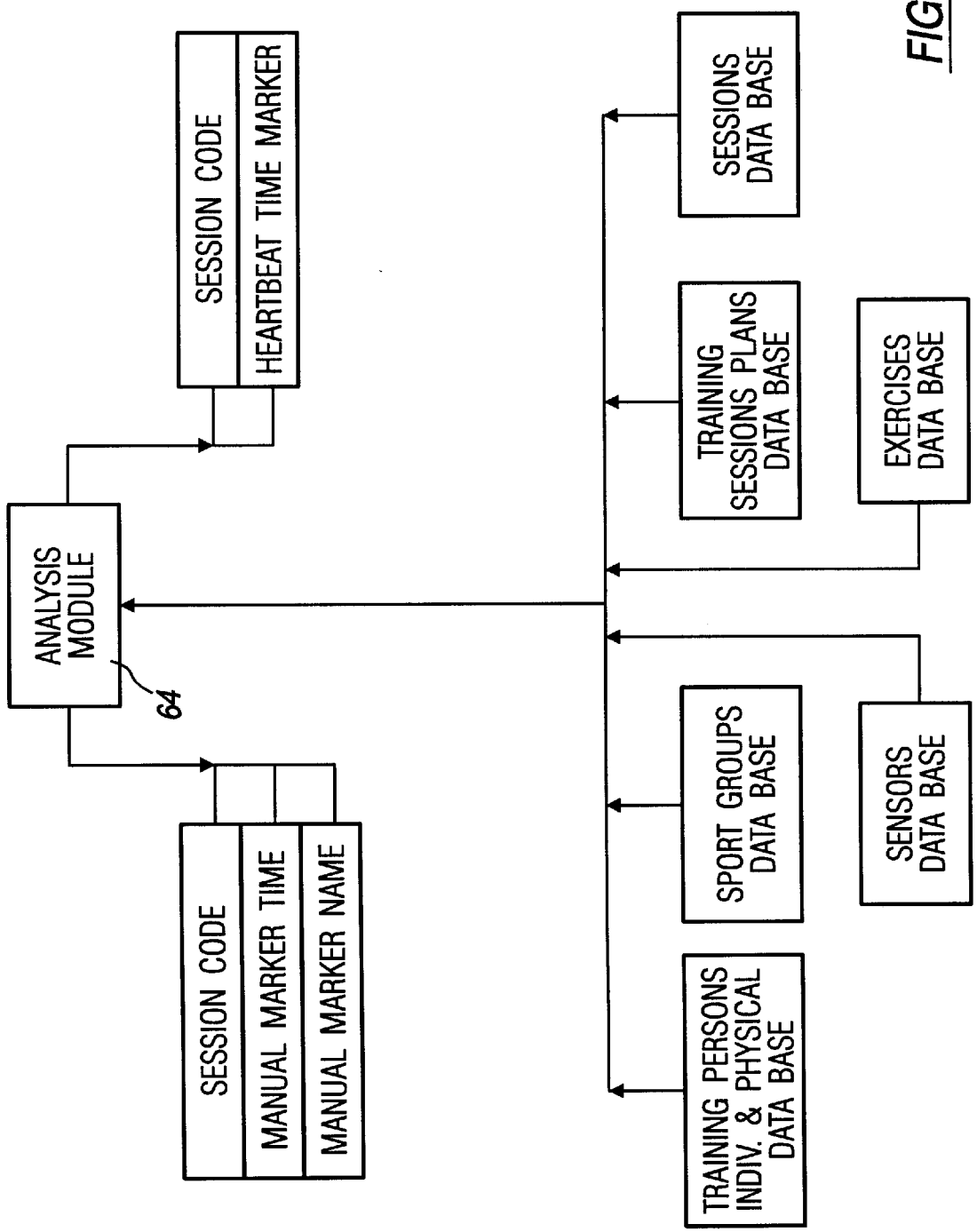
FIG. 12 is a block diagram illustration of an analysis module according to the invention.

Analysis Module 64, illustrated in detail in FIG. 12, is used primarily by PC 50. This module also has access to all the other data bases and performs analyses of various data stored therein according to the PC software, both in real time and over time.

Operation of the system of the present invention is as follows. Data concerning each individual who wishes to utilize the system is entered into his own Personal Data Base. Each individual is given a Bench Test, governed by the computer 50, for deriving an individual coefficient for cost of work per unit of mechanical work. The bench test includes the following steps. An IPDL is fastened on the individual. Computer 50 defines a first load for the individual (i.e., height of step on which he must climb and the step rate at which he must climb up and down) and sends an appropriate command to a buzzer synchronization circuit in the IPDL. Synchronization for a step rate for that load is provided by the IPDL, as by a buzzer buzzing each time a step must be taken. The heart beat data of the individual is monitored in real time in the IPDL and transmitted via the CIU to the computer. The computer calculates a first load performance result from the heart beat data of the individual under the first load, In accordance with the first load performance result, the computer now defines a second load for the individual. An appropriate command for the second load (new step rate) is sent to the IPDL which provides synchronization, as by the buzzer, for the second step rate. Again, the heart beat data of the individual is monitored in real time in the IPDL and transmitted to the computer. The computer calculates a second load performance result from the heart beat data of the individual under the second load. An appropriate command for a third load (preset according to the second load) is sent to the IPDL which provides synchronization, as by the buzzer, for a third step rate. (If the heart rate of the individual goes above 170 under the second load, the bench test is halted without a third load.) Again, the heart beat data of the individual is monitored in real time in the IPDL, transmitted to the computer, and the computer calculates a third load performance result from the heart beat data of the individual under the third load. Finally, the computer derives an individual coefficient for cost of work per unit of mechanical work for the individual, based on the first, second, and third load performance results. It will be appreciated that the heart beats cost of work corresponds to the calories expended by the individual while performing the measured work.

A description of the Bench Test computer program module is as follows:

Description of Bench Test PC Program Module

1. Personal data received (from personal Data Base).
2. Command to IPDL sent: IPDL address, Start Test, 1 start beep, Start IPDL Timer.
3. Starts Rest Timer of Module for "M" rest minutes; Time elapsed represented graphically in Test Window.
4. Reception of Time Marks from client, record to Data base, HRB "rest" is fixed.
    HRB "rest" is fixed when current HRB fluctuations are no more than +/−2 HB/min.
    HRB "rest" is represented in Test Window (as a parameter).
5. Command to IPDL sent at (M−15 sec) time: IPDL address, continue measurement,
    "Be ready" signal—2 beeps (a signal for person to be ready for start of test).
6. First load step frequency calculated: n1=Wrk1/(W*4/3*h), 1/min;
    where:
    Wrk1—first stage load work, kgm/min. Default—300 kgm
    W—a person's weight, kg(lb);
    h—bench height, m (in).
7. Command to IPDL created and sent: IPDL address, Continue Measurement, "n1*4 beeps/min" for "t1" minutes.
8. Reverse IPDL acknowledge reception.
9. First load Timer T1 started for "t1" minutes. Time elapse represented graphically in Test Window.
10. Second load defined: at last 30 seconds of first stage time elapsed—HRB checked. If HRB>80—the second load is Wrk2, if HRB<80—the second load is Wrk2*. Where HRB—Heart Beats per minute.
    Default values for Wrk2 is 600 kgm, for Wrk2* is 900 kgm.
11. Second load step frequency n2 calculated for Wrk2 at same way as in (6).
12. Command to IPDL created and sent as in (7): IPDL address, Continue Measurement, "n2*4 beeps/min for "t2" minutes.
13. Second load Timer T2 started for "t2" minutes. Time elapse represented graphically in Test Window.
14. Third load defined: If Wrk2=600 kgm/min, then Wrk3=900 kgm/min,
    if Wrk2*=900 kgm/min, then Wrk3*=1200 kgm/min.
    (Here Wrk3 and Wrk3* are default values).
14.1 If HRB>170, then 3rd load is cancelled and Command (18) is sent.
15. Third load step frequency n3 calculated for Wrk3/Wrk3* at same way as in (6).
16. Command to IPDL created and sent: IPDL address, Continue Measurement, "n3*4 beeps/min for "t3" minutes. Reverse IPDL acknowledge reception
17. Third load Timer T3 started for "t3" minutes. Time elapse represented graphically in Test Window.
18. After that T3 elapsed, Timer T4 "rest" started. Record to DB.
19. After that T4 elapsed, Command to IPDL sent: "IPDL address, Stop measurement".
20. Calculation of PWC170 performed (Power Work Capacity at 170 Heart Beats per Minute):
    20.1 $PWC170_1=Wrk1+(Wrk2-Wrk1)*(170-HRB1)/(HRB2-HRB1)$,
    20.2 $PWC170_2=Wrk2+(Wrk3-Wrk2)*(170-HRB_2)/(HRB_3-HRB_2)$,
    20.3 $PWC\ 170=½\ (PWC170_1+PWC170_2)$, wt.
    20.4 If there is no 3rd load, then PWC calculated by extrapolation method, from two known points:
        1st point is an average HRB1 versus Wrk1 load, 2nd point is an average HRB2 versus Wrk2 load.
        PWC170 is then defined at HRB=170 Heart Beats per minute.
21. PWC170 as a first personal fitness parameter represented in Test Window and stored in personal Fitness Data Base.

22. Calculation of Pulse Cost for 1 watt.

22.1 Full external work calculated. Wrk=(Wrk1*t1+Wrk2*t2+Wrk3*t3), watt.

22.2 Heart Beats Sum calculated during 3 stages of loads from 1 st load beginning, $HBS_{ext}$.

$$HBS_{ext}=HBS1+HBS2+HBS3-HRBrets*(t1+t2+t3)$$

22.3 Heart Beat Cost for 1 watt calculated. $HBC_{ext}=HBS_{ext}/Wrk$, HB/wt. The result is represented in Test Window: "HBC for 1 watt of external work".

23. Calculation of Pulse Cost for 1 calorie of Total Energy Expenditure, here—TEE is Total Energy Expenditure for Tested Person.

23.1 Calculation of TEE for 1st load: $TEE_1=n1*t1*(0.35+2.4*h)W*5$, cal.

23.2 Calculation of TEE for 2nd load: $TEE_2=n2*t2*(0.35+2.4*h)W*5$, cal.

23.3 Calculation of TEE for 3rd load: $TEE_3=n3*t3*(0.35+2.4*h)W*5$, cal.

23.7 Summarizing of TEE for all loads—SUM(TEE), cal.

23.8 Calculating of REE—Rest Energy Expenditure:

for man—REEm={66.473+13.752*Weight+5.003*H−6.755*Age}, cal/min;

for woman—REEw={65.096+9.563*Weight+1.85*H−4.676*Age}, cal/min.

23.9 Calculating of Pulse Cost for 1 calorie:

$HBC_{cal}=\{HBS_{tot}\}/\{\{SUM(TEE)\}-REE*(t1+t2+t3)\}$, HB/cal.

$HBS_{tot}$=HBS1+HBS2+HBS3, Heart Beats Sum during all 3 loads of test.

The result is represented in Test Window.

24. Calculating of maximal oxygen consumption at maximal Heart Rate—VO2 max.

24.1 Calculated average HR1 during 1st load and a value of $VO2_1=TEE_1/5$, ml of O2.

24.2 Calculated average HR2 during 2nd load and a value of $VO2_2=TEE_2/5$, ml of O2.

24.3 Calculated average HR3 during 3rd load and a value of $VO2_3=TEE_3/5$, ml of O2.

24.4 Using values of 24.1, 24.2, 24.3 and extrapolation routine, calculate a value of VO2 max for a maximal Heart Rate (220−Age).

At the start of a new training session, each individual who does not have an assigned IPDL is given an IPDL for use during the session. Before the session begins, each IDPL is checked to ensure that proper communications exits and that the IPDL is functioning properly. The coach or physiologist indicates the members of the group to be monitored together, which data is saved in the Groups Data Base. He then presses Start and this opens a new monitoring session in the Sessions Data Base for each individual, and data logging of the group or individual begins.

Figure 13:
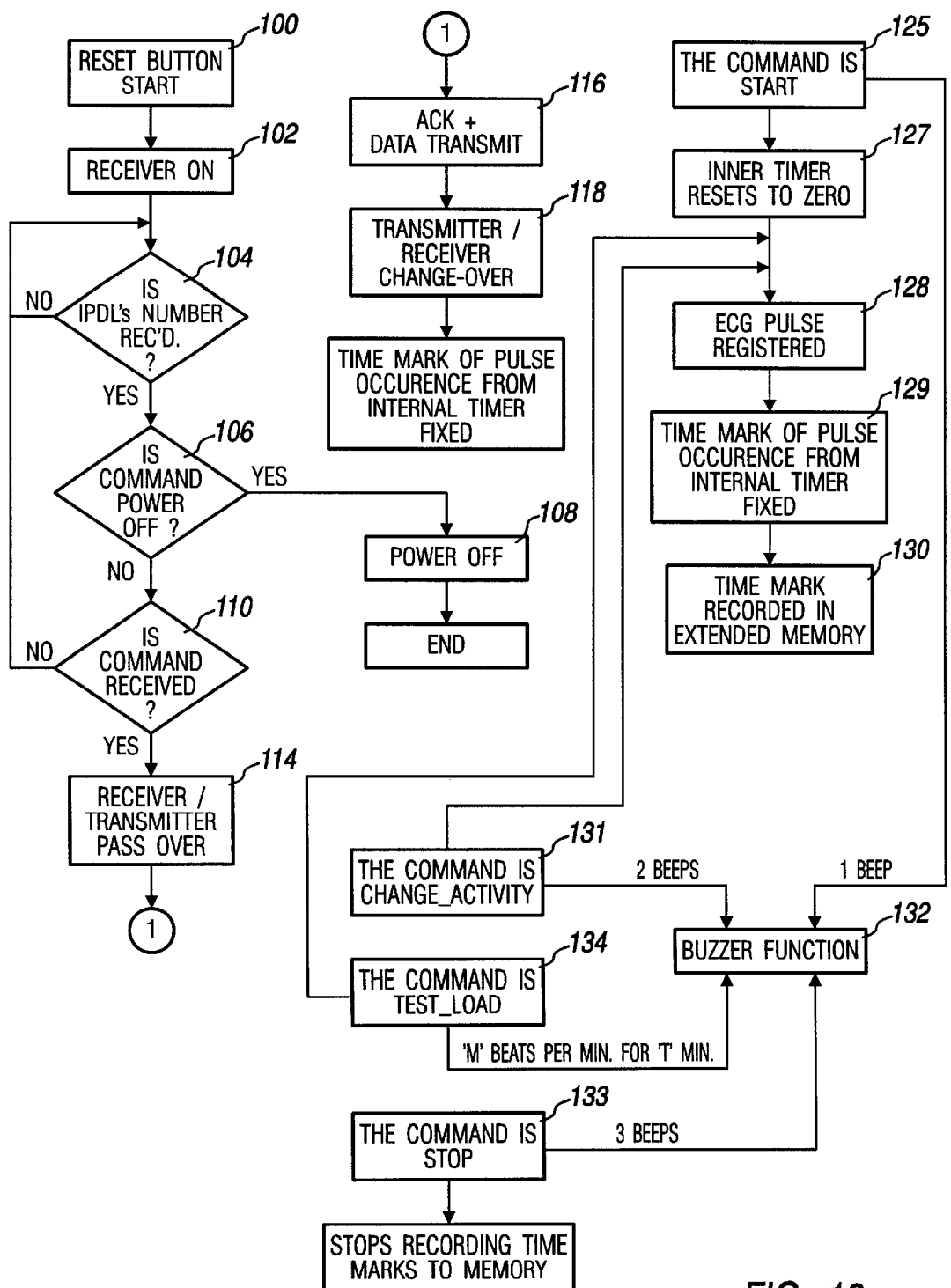
FIG. 13 is a flow chart of the operation of the micro-controller in the individual data logger of FIG. 2.
Figure 14:
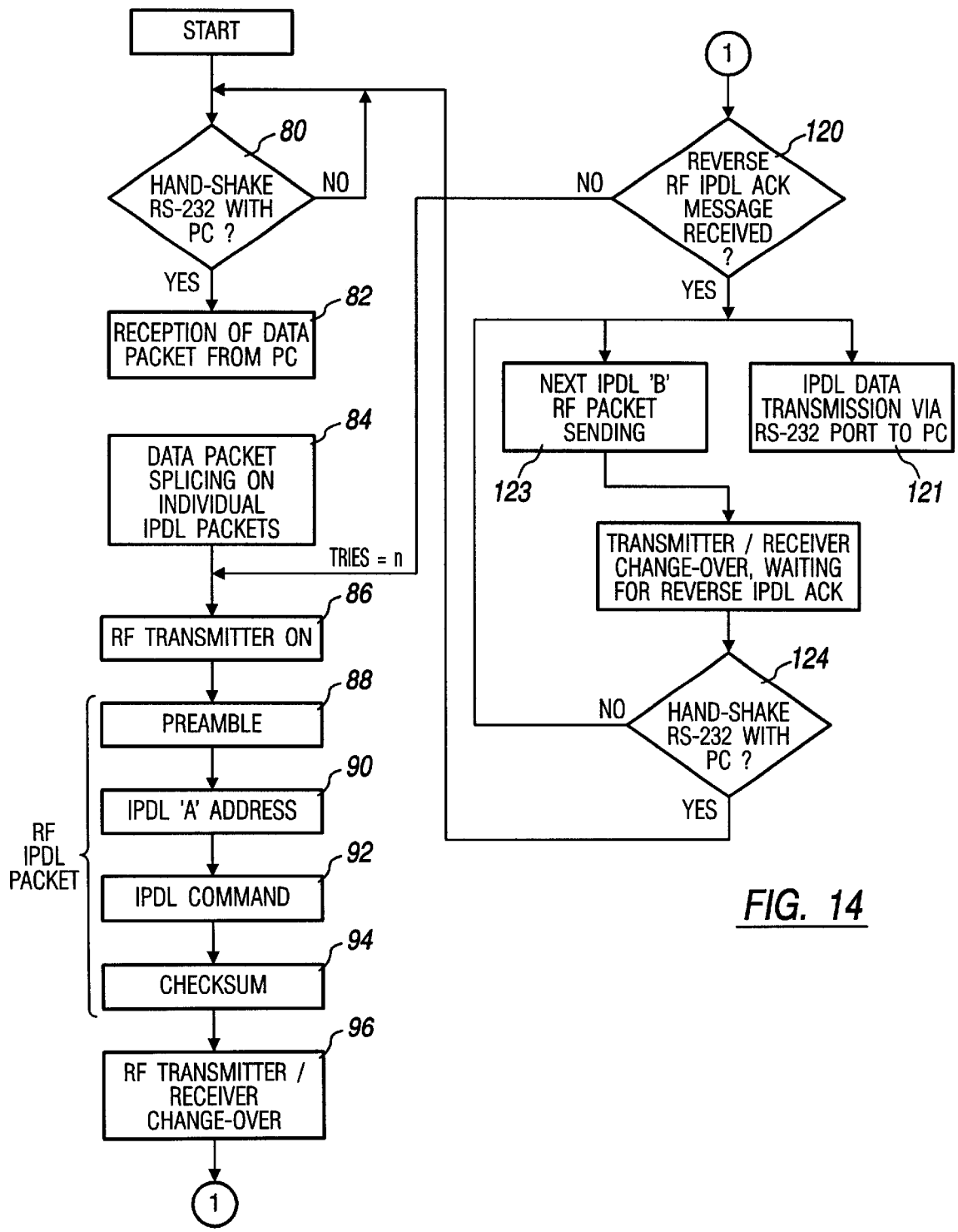
FIG. 14 is a flow chart of the operation of the central interface unit of FIG. 4.

Data logging and preliminary analysis will now be described with reference to FIGS. 13 and 14, flow charts of the operation of the micro-controller in the individual data logger (IPDL) of FIG. 2 and of the operation of the central interface unit of FIG. 4, respectively. CIU 30 determines whether it is connected to PC 50. (FIG. 14, block 80). If yes, it receives from PC 50 a command packet for each pooling cycle of the IPDLs for the session (block 82). Each command packet for current pooling contains a combination of IPDL addresses, for each IPDL which is participating at that moment in a monitoring session, together with the respective command for each IPDL. A list of exemplary IPDL commands is as follows.

Command: "CLIENT_STATUS", the IPDL transfers the status of its battery in a reverse communication—"BATT_LOW" OR "BATT_NORM". The IPDL answer also indicates normal communication.

Command: "START" (block 125 in FIG. 13), the IPDL provides an audible sound, i.e., 1 beep (reference 126), resets its timer to zero (block 127), and starts recording time marks of each heart beat to its extended memory (blocks 128, 129, 130).

Command: "CLIENT_MEASUREMENT", the IPDL continues measurement, continues performance of a previous command, transfers all time marks content of its memory to the CIU.

Command: "CHANGE_ACTIVITY" (block 131), the IPDL provides an audible sound (block 132), i.e., 2 beeps, to signal to the user to change to the next activity. The IPDL continues measurement, and transfers all time marks content of its memory to CIU.

Command: "STOP" (block 133), the IPDL provides an audible sound, i.e., 3 beeps, to signal to the user to stop. The IPDL stops measurement, and transfers all time marks content of its memory to the CIU.

Command: "TEST_LOAD" (block 134), the IPDL provides an audible sound with a frequency of 'N' beeps per minute for 't' minutes, continues measurement, transfers all time marks content of its memory to the CIU.

Command: "SHUT_DOWN". the IPDL shuts down its power.

Generally, a command packet from the computer to the CIU looks as follows:

Preamble, Command (for CIU), Command Packet (A1C1, A2C2, A3C3, ... A25C25), wherein A1 ... A25 are IPDL addresses, and C1 ... C25 are respective commands for each IPDL.

After receiving the pooling Command Data Packet from PC 50, CIU 30 slices the data packet according to the individual IPDL address, with its corresponding commands (block 84), and prepares this data for RF transmission. CIU 30 activates its transmitter (block 86) and transmits a direct data message to a first IPDL. Each IPDL packet includes a general preamble (block 88), the IPDL address (block 90), the command for that IPDL (block 92), and a check sum (block 94). Then, CIU 30 changes-over its transceiver to the receiving mode (block 96) and awaits receipt of an acknowledgement message from the IPDL.

In the meantime, the individual turns on the IPDL (FIG. 13, block 100), and puts it on his chest. The IPDL receiver is in receiving mode (block 102) and receives all incoming data. When the IPDL identification number is received (block 104), the associated transmitted command is entered in the IPDL buffer. If the command is POWER OFF (block 106), the IPDL turns off (block 108) and the operation ends. IPDL 10 is shut down after a pre-determined number of idle minutes of no transmissions received and no measurement of heart beats, or upon receipt of a specific command from the computer to shut down.

Upon receipt of a command (block 110), the IPDL begins to carry out the command (block 112). At the same time, the IPDL changes the transceiver to the transmitting mode (block 114) and transmits an acknowledgement of receipt of the data packet (block 116). The acknowledgement generally includes a general preamble, the IPDL address, the last received command, full content of data buffer (heart beat data), and a check sum. The IPDL transceiver now changes over to receiving mode (block 118).

Upon receipt of the acknowledgement from CIU 30 (block 120), the CIU resends the content of the IPDL data buffer, together with the corresponding IPDL address and last command, via RS232 port to PC 50 (block 121). If the CIU does not receive an acknowledgement, it waits 'm' milliseconds and then resends the previous RF direct message to the same IPDL (reference 122). The CIU tries to send a preset number of tries ('n'), and then sends a signal to the PC that the IPDL is out of contact.

After a pre-set number of tries, and without regard to whether the IPDL answered or not, the CIU sends the appropriate RF packet to the next IPDL (block 123), in the same way as described above with reference to the first IPDL. In this way, the CIU is pooling and maintaining contact with all working IPDL's of each session, until it completes a full pooling cycle which is prescribed by the command packet received from the PC (block 124). Then the CIU turns to the RS232 to receive the next pooling command packet from the PC, and starts the pooling process again from the beginning. It will be appreciated that each pooling command packet can include different commands for each IPDL, such that each command packet is likely to be different from the others.

The description above relates to operation of IPDL 10 in a group mode. It will be appreciated that IPDL 10 can also operate in an independent mode. In this case, the IPDL is activated by pressing the reset button when the individual begins work. When the IPDL is placed in contact with the chest of the individual, the ECG measuring apparatus will begin to measure pulses and the IPDL will remain on and operative to record heart beat data. This will continue until the individual turns off the IPDL (i.e., by removing the unit from his chest) or until RF contact is made with CIU 30. In any case, the heart beat data remains stored in the IPDL memory until a specific request is received from CIU 30 and the data is successfully transmitted.

Figure 15:
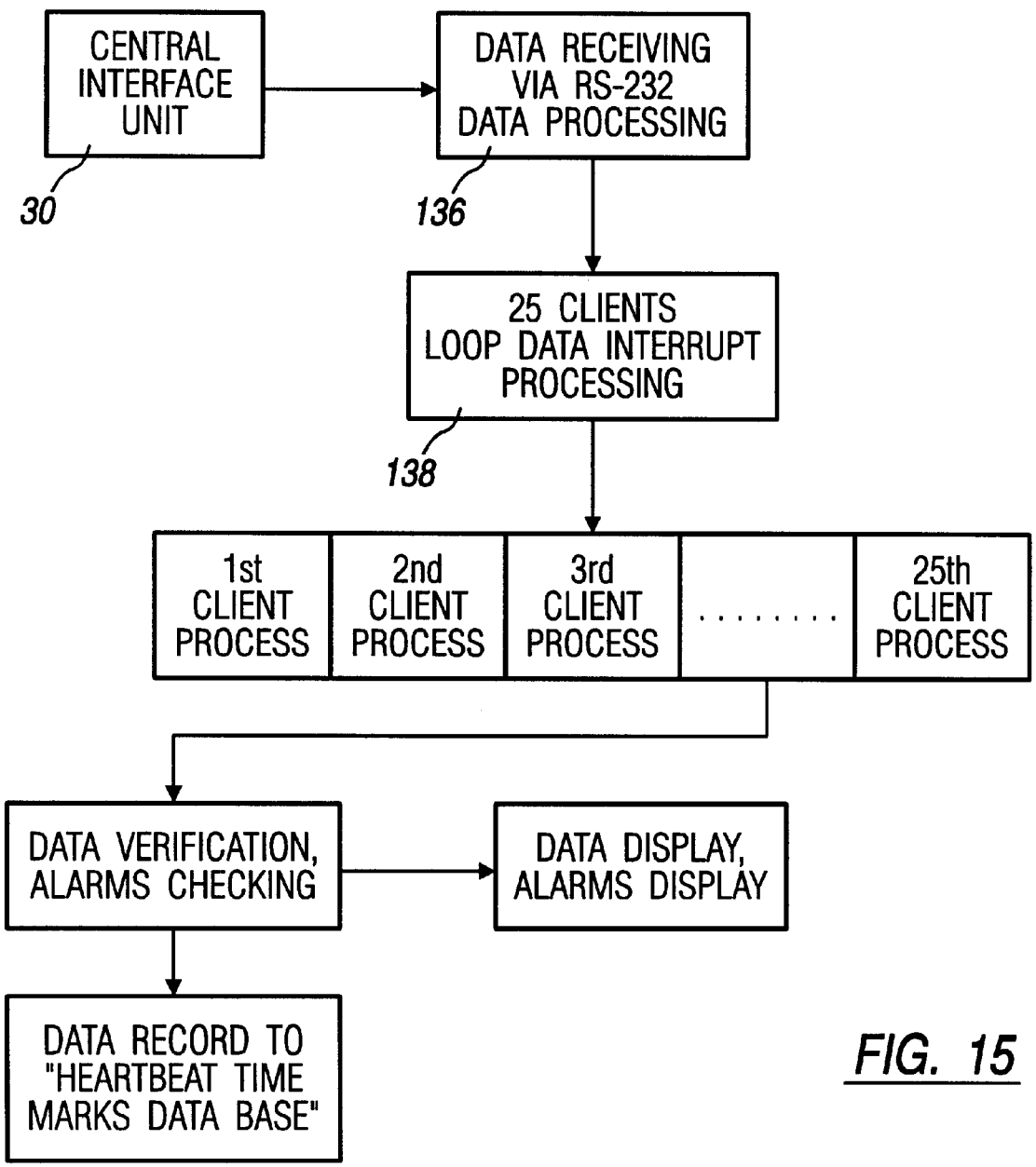
FIG. 15 is a block diagram illustration of the monitoring process according to a preferred embodiment of the invention.

The PC program monitoring process according to a preferred embodiment of the invention is illustrated schematically in FIG. 15. According to this embodiment, 25 individuals are monitored simultaneously by a single PC. Data from each of 25 IPDLs is received in CIU 30 and transferred as a general stream of data to the PC for processing (blocks 136, 138).

Figure 16:
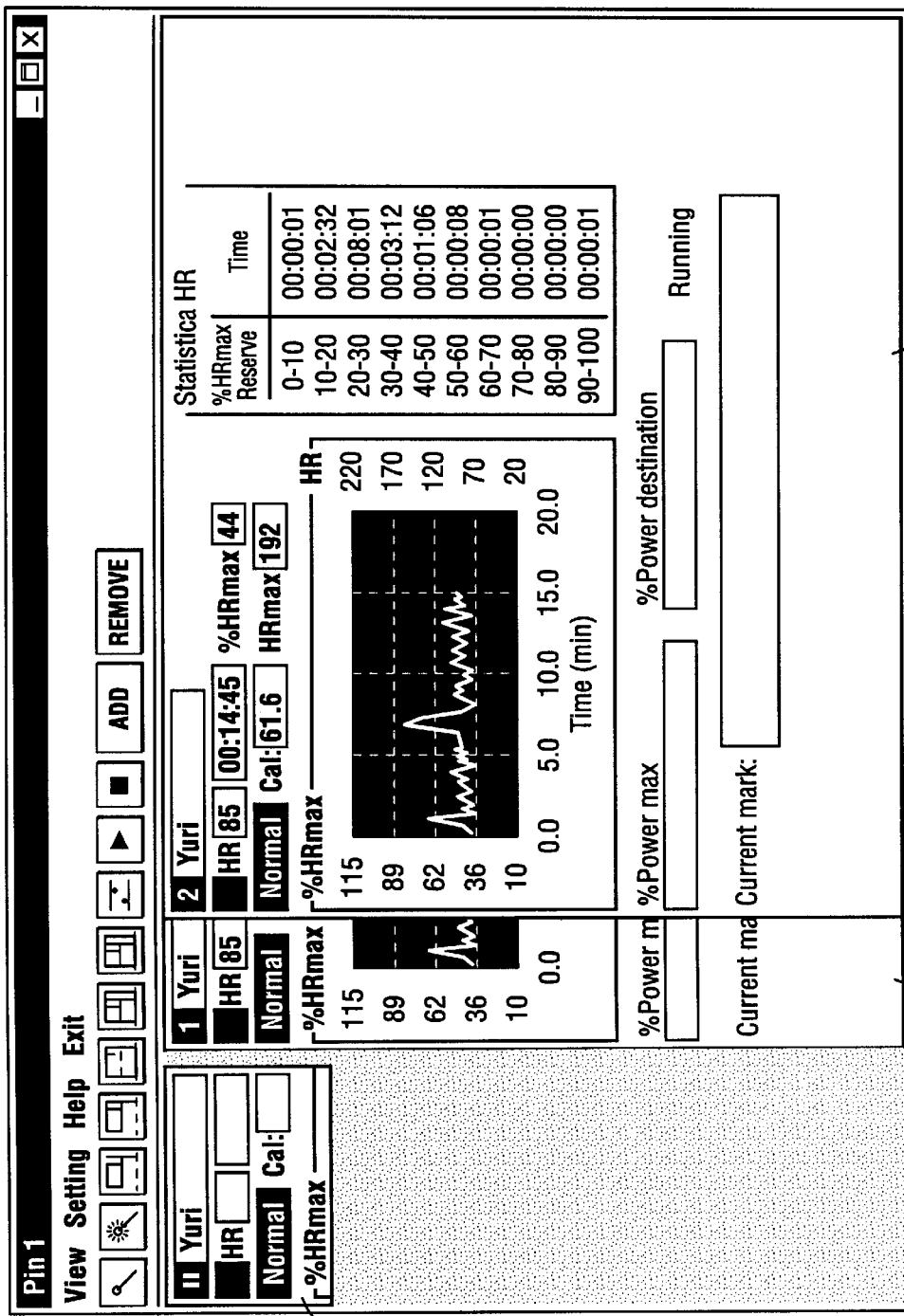
FIG. 16 is an example of a PC window in the monitoring process of FIG. 15.

One example of a display screen is shown in FIG. 16. As can be seen, screen 140 is divided so as to present data regarding between 1 and 25 individuals simultaneously. In a minimum window 142, for example, the name of the individual, his heartbeat rate, and an indication whether this is normal for this individual or not, are shown. When necessary or desired, the window can be expanded partially 144 or fully 146, as by a click of a mouse button, to display any selected parameters relating to the individual's performance during the session, all updated on-line in real time throughout the session. These parameters can include heart beat rate, maximum heart rate for this individual, percentage of maximum heart rate at which the individual is working at the present time, heart beats cost since the start of the session, the total target heart beats cost for the session, a graphical illustration of the heart rate over time, and any other statistics which are useful during the session for helping the coach control a group of trainees.

In addition, warning signals are shown in any case where a preset marker (either automatic or inserted by the coach) is actuated. In such a case, a visible or audible flag is provided in the window of the relevant individual, or the window itself can change color depending upon the type of alarm. At this point, his or her window can be expanded so as to permit viewing of all the personal data from that session. It is also possible to retrieve other personal information about the individual during the session without interrupting the session.

Figure 17A:
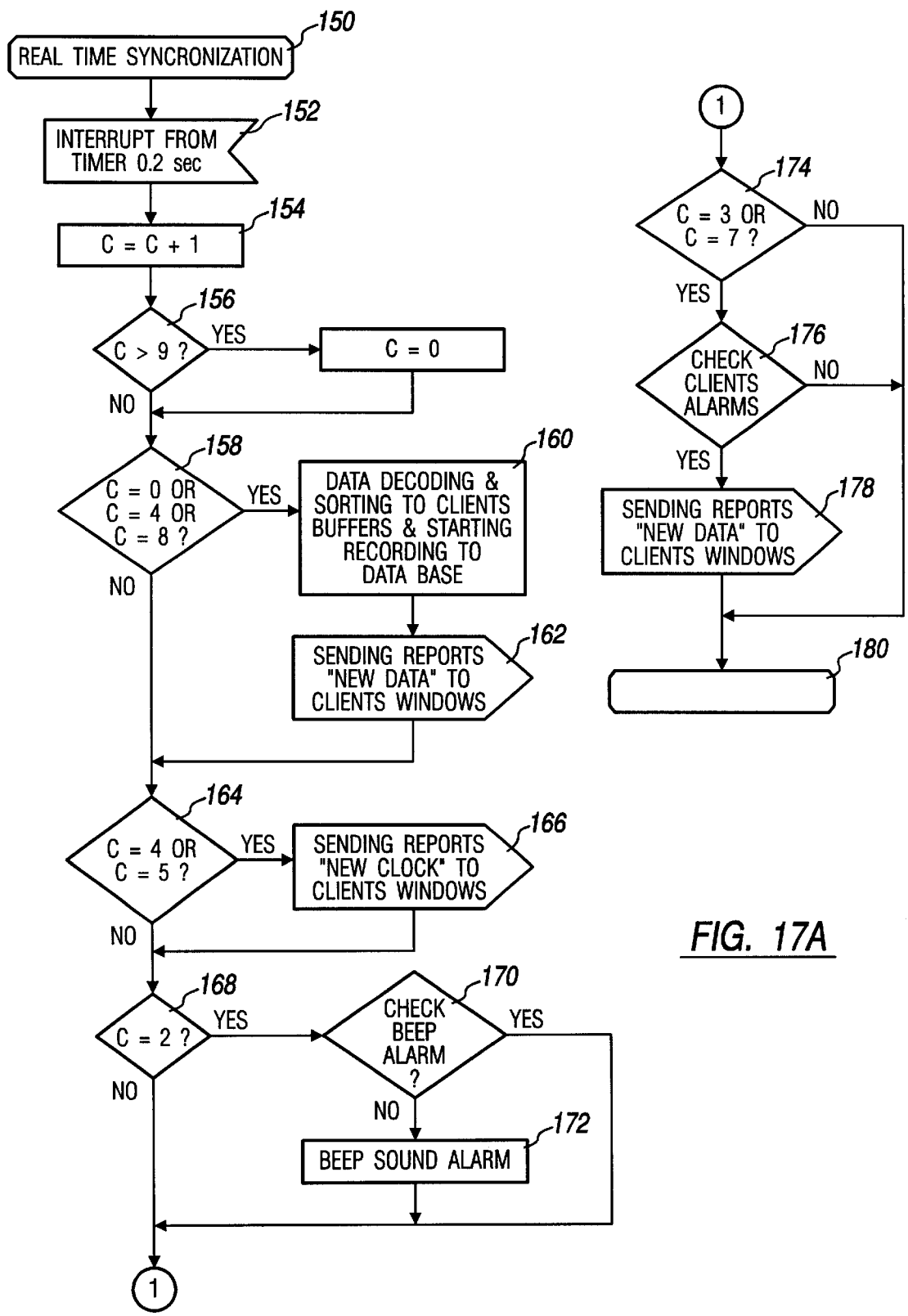
FIGS. 17A and 17B are is a flow chart of the monitoring operation of the PC arrangement of FIG. 5 in real time.

FIG. 17A is a flow chart of a few of the unique monitoring operations of the computer 50 in real time. It will be appreciated that the computer carries out a variety of functions at the same time, including imaging, inputting data, calculations, etc. Synchronization is needed so that each operation begins at the correct time, in the proper order, so as not to waste PC processor resources. It is a particular feature of the invention that the computer functions as a plurality of separate virtual computers.

In FIG. 17A, the operation begins with real time synchronization (block 150). In the illustrated embodiment, one complete cycle is 2 seconds, although a cycle of any other predetermined duration can, alternatively, be utilized. Thus, in this embodiment, the computer waits, with an interrupt from the timer every 0.2 seconds (block 152), and then a counter C is raised by one number (block 154). If C is greater than 9 (block 156), then C is reset to 0. If not, and if C equals 0, 4, or 8, (i.e., after every second) (block 158), the computer asks RS 232 whether any data is waiting. If yes, the data is decoded, sorted and stored to the appropriate clients' (exercising individuals') data bases (block 160). A report is sent to update the clients' window on the display according to the most recent data (block 162), as described below.

If C is 1 or 5 (block 164), the computer sends a report to display a new clock (block 166) to the clients' (exercising individuals') window on the display, as described below. If C is 2 (block 168), the computer checks (block 170) whether all parameters are within limits for all individuals. If not, a beep alarm is sounded (block 172), to alert the coach. If C is 3 or 7 (block 174), the computer checks each client's alarms (block 176) and sends a report to change the display (block 178) for each client who has exceeded a limit or activated a manual marker. When the cycle is completed, the computer begins the next process state (block 180).

Figure 17B:
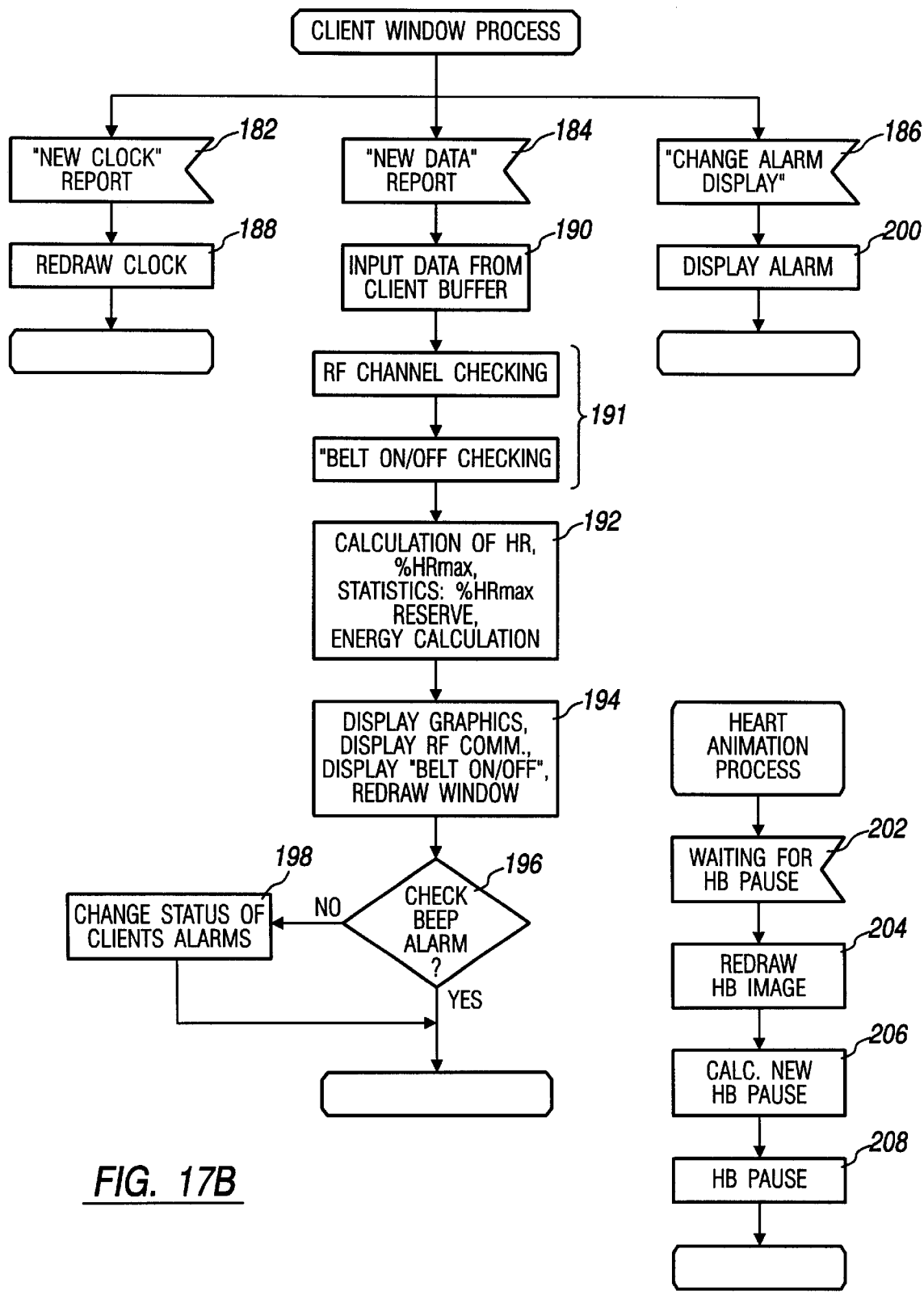

Referring to FIG. 17B, there are shown block diagrams of a Client Window Process and Heart Animation Process. In the Client Window Process, the computer waits to receive a new clock report (block 182), a new data report (block 184), or a report to change alarm display (block 186). When a report to change the clock is received, the clock on the display is redrawn (block 188), and the computer moves to the next process state. When a report of new data is received, the data is input from the individual's data base (block 190). The computer checks that communication exists with all the IPDLs (blocks 191). The computer now processes the data (block 192), performing a variety of predetermined calculations, including calculation of heart rate, percentage of heart rate maximum, various statistics, such as percent of heart rate max reserve, and energy calculation. Some or all of this data can now be displayed graphically (block 194), and the computer redraws the individual window. The computer checks to ensure that the individual is exercising within his predefined limits (block 196). If not, a message is sent to change the status of the client's alarms (block 198). If all parameters are within the proper range, the computer moves to the next process state.

The Heart Animation Process begins by waiting for a heart rate interval (block 202). When received, the heart rate image (such as a pulsing heart shape) is redrawn (block 204) and the new heart rate interval is calculated for the last received heart beat (block 206). The heart beat pause is registered in block 208, and the computer moves to the next process state.

It will be appreciated that there are numerous other process states, in addition to the process states described above. However, these are conventional process states required for operation of the system. Similarly, a number of programs can carry out the steps described above. However, all these are well known to programmers skilled in the art.

Figure 18:
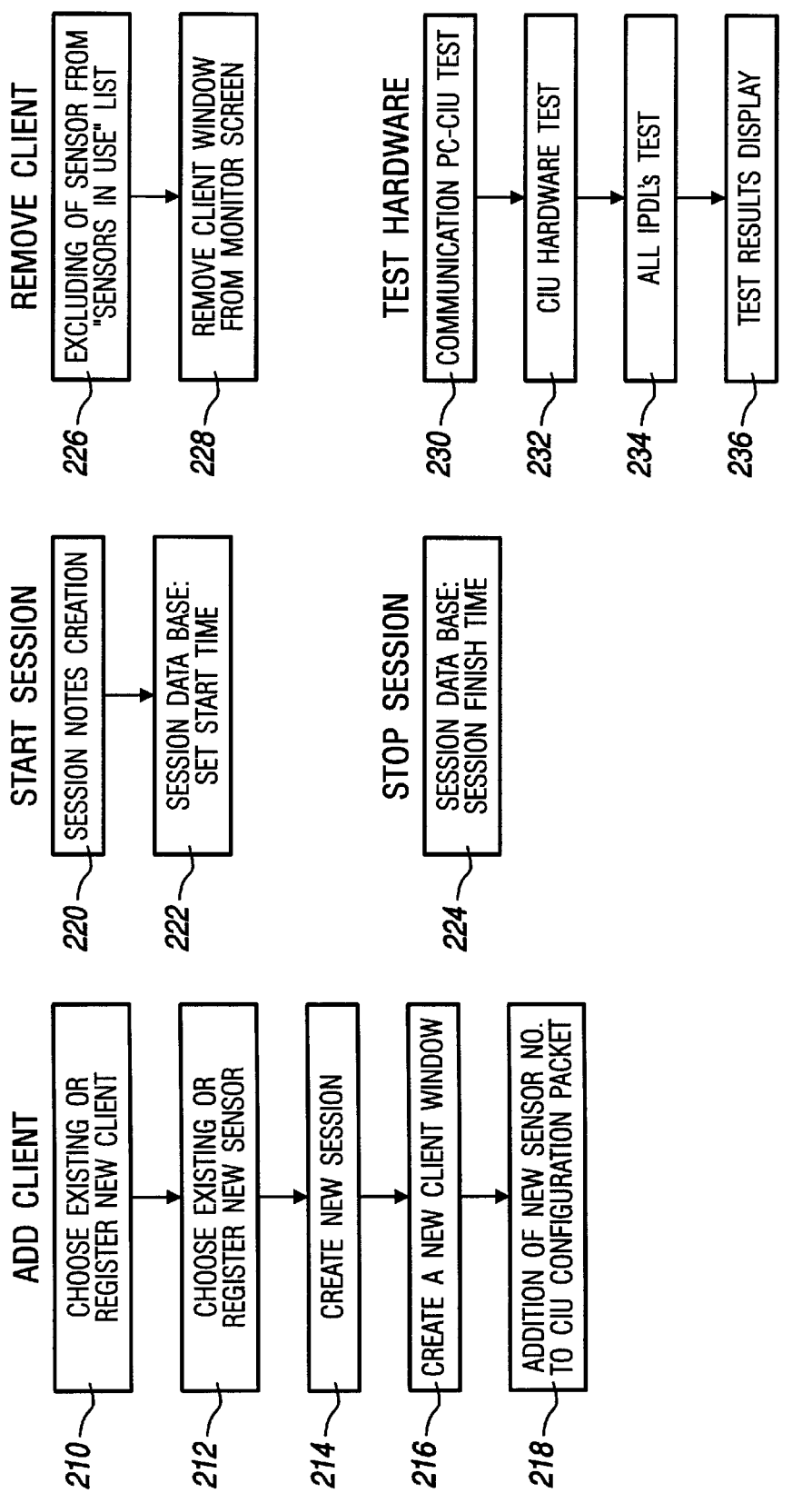
FIG. 18 is a block diagram of monitor module manual controls in the monitoring operation of FIGS. 17A and 17B.

FIG. 18 is a block diagram of monitor module manual controls in the monitoring operation of FIG. 17A and FIG. 17B. Add client shows how to add another individual to the system. First, an existing client is selected, or a new client is registered (block 210). An existing sensor is indicated or a new sensor is registered (block 212). When the individual begins work, a new monitoring session is created (block 214), and a new client window is opened (block 216). Finally, the new sensor number is added to the CIU configuration packet (block 218). When a client stops exercising, the sensor is removed from the list of sensors in use (block 226) and the client window is removed from the monitor screen (block 228).

When a monitoring session is started, the creation of a new session is noted (block 220) and the start time of the session is set in the session data base (block 222). When the session ends, the session finish time is set in the session data base (block 224).

Testing of the hardware is carried out by testing communication between the computer 50 and the CIU 30 (block 230). Then, the CIU hardware is tested, to ensure proper functioning (block 232). Each IPDL is tested to ensure that communication exists (block 234), and the test results are displayed (block 236) so the coach can verify that all is in order before proceeding.

Figure 19:
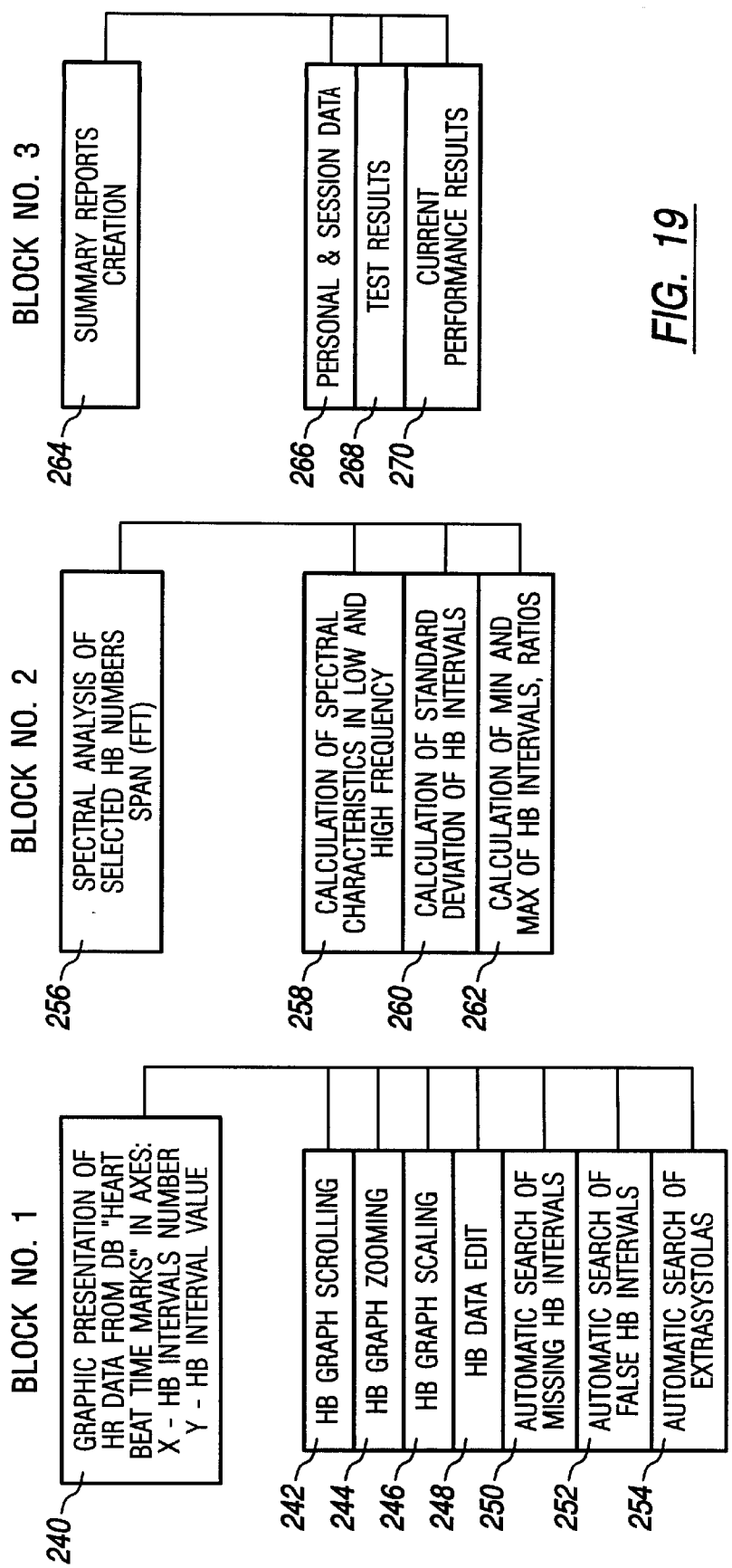
FIG. 19 is a flow chart of the analysis operation of the PC arrangement of FIG. 5.

FIG. 19 is a flow chart of various analysis operations of the computer of FIG. 5. Block No. 1 (block 240) illustrates preparation and viewing of a graphic presentation of the heart beat data stored in the Heart Beat Time Marks Data Base. The graph in the illustrated embodiment is a plot of heart beat interval number vs. heart beat interval value (time). The graph can be viewed and manipulated by the coach in a variety of ways, which are provided by the computer. There is preferably scrolling (block 242) and zooming (block 244), and there can be scaling of the graph (block 246). The data can be edited (block 248). In the embodiment where heart beat data is associated with an identifier, the computer is programmed to search for missing intervals (block 250). It can also search for false heart beat intervals (block 252). Preferably, it can also search for extrasystolas (block 254). These data cannot be found from conventional measurement of heart rate.

Block No. 2 (block 256) is concerned with the spectral analysis of a selected heart beat span. This analysis is carried out by the use of a Fast Fourier Transform. This is done by calculating the spectral characteristics of the heart beat interval data in low and high frequency (block 258), calculation of standard deviation of heart rate intervals (block 260), and calculation of minimum and maximum heart beat intervals, as well as necessary ratios (block 262).

Block no. 3 (block 264) shows creation of summary reports. Summary reports can be created using personal and session data (block 266), various test results of the individual (block 268), and results of the individual's current performance (block 270).

It will be appreciated that these are but a few examples of special analysis functions performed by computer 50. Other analyses, including conventional heart rate calculations, and analyses over time of the individual's performance and fitness levels, can be easily included.

What is claimed is:

1. A system for simultaneous monitoring of a plurality of individuals comprising:
    an individual physiological data logger (IPDL) for each individual for measuring and storing heart beat data, the IPDL including:
        an electro-cardiogram (ECG) measuring device for providing heart beat data;
        an extended memory for storing said measured heart beat data;
        a synchronization element;
        a micro-controller including a synchronization element controlling circuit; and
    RF transceiver apparatus;
    a central interface unit selectably couplable by radio telemetry communication to each IPDL for transmitting thereto a plurality of commands and for receiving therefrom said heart beat data; and
    a computer coupled to said central interface unit for providing commands for each said IPDL, for performance of an individual bench test for deriving an individual conversion coefficient of heart beats cost per unit of mechanical work, and for monitoring and analyzing, in real time, said heart beat data, utilizing said individual coefficient of heart beats cost per unit of mechanical work, of each of the plurality of individuals, wherein said computer scans said heart beat identification data during analysis and commands said central interface unit to request re-transmission of any missing heart beat data.

2. The system of claim 1, wherein:
    said ECG measuring device includes a printed circuit board, for measuring electrical activity of the heart muscle as detectable on the chest; and
    said IPDL further includes:
        a clock for providing time marks;
        software for operating RF transceiver apparatus for RF communication with said central interface unit (CIU); and
        an electric power source.

3. The system according to claim 1, wherein said computer further includes means for analyzing and storing data about each individual in real time and over time.

4. A system for simultaneous monitoring of a plurality of individuals comprising:
    a plurality of individual physiological data loggers (IPDL), each for coupling to an individual, each having an ECG measuring device for providing heart beat data of said individual, and an extended memory, for producing and storing an output representative of said heart beat data
    a central interface unit including RF transceiver apparatus for sequentially transmitting a predetermined signal to cause each of said plurality of IPDLs to transmit IPDL identity data and stored heart beat data, for receiving these transmissions, and for requesting re-transmission of any missing heart beat data; and
    a computer for analyzing and displaying, in real time, said heart beat utilizing a calculated conversion coefficient of individual heart beats cost of specific mechanical work, together with identification and personal data for said individual each of the plurality of individuals.

5. The system according to claim 1, wherein each said IPDL provides heart beat data as time marks, the absolute time from the start of exercise at which a heart beat pulse signal is received.

6. The system according to claim 1, wherein each said IPDL provides heart beat data as relative time intervals between each heart beat, together with heart beat identification data.

7. The system according to claim 1, wherein said computer includes a plurality of data bases, selected from a Personal Data Base; a Fitness Data Base; a Groups Data Base; a Sensor Data Base; a Training Session Plans Data Base; a Sessions Data Base, for details about each session; a Heart Beat Time Marks Data Base; a Manual Coach Markers Data Base; and an Exercises Data Base.

8. The system according to claim 1, wherein said computer includes an plurality of software modules selected from a group including: a Sensor Registration Module; a Person Editor Module; a Group Editor Module; a Session Creation Module; a Training Plan Editor Module; a Monitor Module; and an Analysis Module.

9. The system according to claim 1, wherein said central interface unit (CIU) includes:
   a microprocessor;
   RF transceiver apparatus for communication with said IPDLs;
   a power source; and
   a communication circuit for coupling to said computer.

10. The system according to claim 1, further including means for calculating heart beat intervals and spectral analysis of the variability of heart rate.

11. A method for monitoring the activity level and the physiological status of an individual, or a group of individuals, including the steps of:
   measuring heart beat pulses in an individual physiological data logger (IPDL) worn adjacent the chest of an individual;
   calculating heart beat data in said IPDL;
   storing said heart beat data in said IPDL;
   transmitting a command via RF transceiver apparatus from a central interface unit (CIU) to said IPDL in response to a command to transmit said stored heart beat data;
   transmitting said stored heart beat data via RF transceiver apparatus from said IPDL to said CIU;
   transferring said heart beat data from said CIU to a computer;
   analyzing and processing said heart beat data in said computer in real time utilizing an individual coefficient of heart beats cost per unit of external work, and providing an output display, in real time, corresponding thereto.

12. The method according to claim 11, wherein said steps of measuring through analyzing are performed in real time while said individual is performing physical exercise, and wherein said step of analyzing includes calculating individual heart beats cost for performing said physical exercise and providing an output display corresponding thereto.

13. The method according to claim 11, wherein said steps of measuring through storing are performed simultaneously by a plurality of IPDLs, each worn on a different individual; and
   said steps of transmitting are performed sequentially for each of said IPDLs.

14. The method according to claim 11, wherein said individual coefficient for cost of work is derived by means of a bench test including the following steps:
   fastening an IPDL on the individual;
   defining a first load for the individual;
   providing synchronization by said IPDL for a step rate for that load;
   monitoring in real time in said IPDL heart beat data of the individual;
   calculating a first load performance result;
   defining a second load for the individual;
   providing synchronization by said IPDL for a step rate for said second load;
   monitoring in real time in said IPDL heart beat data of the individual; and
   calculating a second load performance result;
   calculating said individual coefficient for cost of work for the individual based on said first and second load performance results.

15. The method according to claim 14, further including, after said step of calculating a second load performance result, the steps of:
   defining a third load for the individual;
   providing synchronization by said IPDL for a step rate for said third load;
   monitoring in real time in said IPDL heart beat data of the individual; and
   calculating a third load performance result;
and wherein said step of calculating said individual coefficient includes calculating said individual coefficient for cost of work for the individual based on said first, second, and third load performance results.

16. The method according to claim 14, wherein said step of providing synchronization includes providing an audible signal at the rate of said step rate.

17. The method according to claim 11, further comprising the step of providing a graphic presentation of the analyzed heart beat data.

18. The method according to claim 11, wherein said computer starts a monitoring session for an individual upon an input command, and analyzed heart beat data for that individual from said session is stored in association with identification data for said monitoring session.

19. The method according to claim 11, wherein said computer starts a plurality of monitoring sessions, each for one of a plurality of individuals, upon an input command, and analyzed heart rate beat data for each individual from said respective monitoring session is stored in association with identification data for the associated monitoring session.

20. The method according to claim 11, further comprising the steps of:
   coupling an unused IPDL to a new individual;
   measuring and storing heart beat data for said new individual in said IPDL;
   starting a monitoring session for said new individual in said computer; and
   causing said computer to actuate said CIU to request transmission of the stored heart beat data from said IPDL, without interrupting other existing sessions.

21. The method according to claim 20, further comprising the steps of:
   opening, on a monitor screen, a new client window when said monitoring session is started; and
   adding a sensor number corresponding to said unused IPDL to a CIU command packet for current pooling.

22. The method according to claim 11, further comprising the steps of:
   removing an IPDL from one of the plurality of individuals;
   ending said monitoring session for that individual in the computer, without interrupting other existing sessions; and
   closing, on a monitor screen, a client window associated with said individual.

23. The method of claim 11, wherein a micro-controller unit in each said IPDL manages two way, half-duplex RF communication between said IPDL and said CIU, heart beat storage upon command from a computer program, providing an audible signal at the start and stop of exercises, and synchronization of rhythmical beeping during a Bench Test.

24. The method of claim 11, wherein said computer calculates heart beat intervals, and utilizes Fast Fourier Transform to perform spectral analysis of the variability of the heart beat rate.

25. The method according to claim 11, including the steps of sending a command packet for current pooling, containing an IPDL address for each IPDL participating at that moment in a monitoring session, together with a respective command for each IPDL, from said computer to said CIU;

slicing said command packet in said CIU according to each individual IPDL address, with its corresponding command;

preparing said data for RF transmission;

transmitting a direct data message sliced from said command packet to a first IPDL; and awaiting receipt of an acknowledgement message from said first IPDL.

26. The method according to claim 25, further comprising the steps of transmitting a direct data message sliced from said command packet to a second IPDL regardless of receipt of an acknowledgement message from said first IPDL; and awaiting receipt of an acknowledgement message from said second IPDL.

27. The method according to claim 11, wherein said IPDL provides heart beat data together with heart beat identification data via said CIU to said computer;

said computer scans said heart beat identification data during analysis and commands said CIU to request re-transmission of any missing heart beat data.

28. The method according to claim 11, further including:

preparing a training program including a combination of specific external work, consisting of different sport activities over different periods of time;

assigning said training program to an individual;

converting values of said external work to personal heart beats cost, using an individual coefficient for cost of work (heart beats cost); and displaying representatives of said personal heart beats cost in a personal Monitoring Window as a personal target power expenditure for performing said training program.

29. The method according to claim 11, wherein said steps of measuring and storing heart beat data is performed at one time, and said step of transmitting said heart beat data to said CIU is performed at a later time.

\* \* \* \* \*